Figure 1:
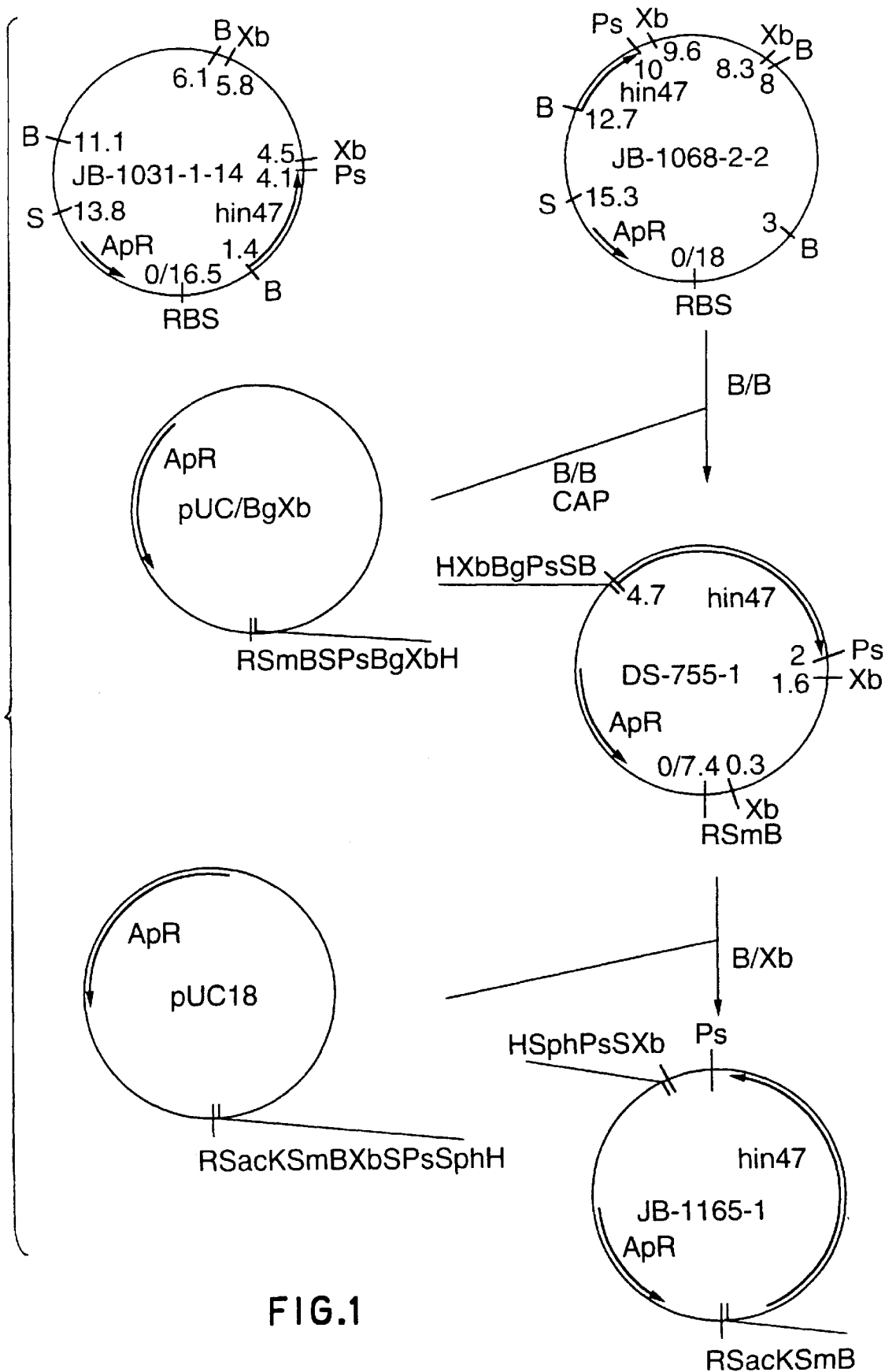

United States Patent [19]
Loosmore et al.

[11] Patent Number: 5,962,430
[45] Date of Patent: Oct. 5, 1999

[54] ANALOG OF HAEMOPHILUS HIN47 WITH REDUCED PROTEASE ACTIVITY

[76] Inventors: Sheena M. Loosmore, 70 Crawford Rose Drive, Aurora, Ontario, Canada, L4G 4R4; Yan-Ping Yang, Apt. 1709, 120 Torresdale Avenue, Willowdale, Ontario, Canada, M2R 3N7; Pele Chong, 32 Estoril Street, Richmond Hill, Ontario, Canada, L4C 0B6; Raymond P. Oomen, R.R. No. 1, Schomberg, Ontario, Canada, L0G 1T0; Michel H. Klein, 16 Munro Boulevard, Willowdale, Ontario, Canada, M2P 1B9

[21] Appl. No.: 08/801,499

[22] Filed: Feb. 18, 1997

Related U.S. Application Data

[60] Division of application No. 08/482,816, Jun. 7, 1995, which is a continuation-in-part of application No. 08/278,091, Jul. 21, 1994, Pat. No. 5,506,139.

[51] Int. Cl.[6] ...................... A61K 39/102; A61K 31/495; A01N 43/48
[52] U.S. Cl. ........................................... 514/44; 424/256.1
[58] Field of Search ........................... 514/44; 424/204.1, 424/206.1, 256.1

[56] References Cited

FOREIGN PATENT DOCUMENTS

| | | |
|---|---|---|
| WO 92/10936 | 7/1992 | WIPO . |
| WO 92/11367 | 7/1992 | WIPO . |
| WO 94/00149 | 1/1994 | WIPO . |
| WO 94/12641 | 6/1994 | WIPO . |

OTHER PUBLICATIONS

Zangwill et al, 1993 MMWR 42:1–15.
Schoendorf et al, 1994 Pediatrics 93:663–8.
Brenner et al, 1988 Nature 334:528–530.
O'Hagan 1992 Clin. Pharmokinet. 22:1–10.
Ulmer et al, 1993 Curr. Opinion. Invest. Drugs 2:983–989.
Chang et al, 1978 Nature 275:617.
Goeddel et al, 1980 Nucl. Acid. Res. 8:4057.
Harkness et al, 1992 J. Bacteriol. 174:2425–2430.
Loeb et al, 1987 Infec. Immun. 55:2612–2618.
Holmes and Quigley 1981, Analyt. Biochem. 114:193–197.
Young and Davis 1985, Gene 38:31–38.
Panezutti et al, 1993 Infec. Immun. 61:1867–72.

*Primary Examiner*—David Guzo
*Attorney, Agent, or Firm*—Sim & McBurney

[57] ABSTRACT

An isolated and purified analog of *Haemophilus influenzae* Hin47 protein has a decreased protease activity which is less than about 10% of that of natural Hin47 protein and preferably substantially the same immunogenic properties as natural Hin47 protein. An isolated an purified nucleic acid molecule encoding the Hin47 analog may be provided in a recombinant plasmid which may be introduced into a cell which is grown to produce the Hin47 analog. Immunogenic compositions comprising the Hin47 analog and the encoding nucleic acid may be formulated as vaccines for in vivo administration to a host, including a human, to confer protection against diseases (caused by a bacterial pathogen, including Haemophilus species, such as *Haemophilus influenzae*, that produces Hin47 protein or a protein capable of inducing antibodies in the host specifically reactive with Hin47 protein. The Hin47 analog and the encoding nucleic acid also may be employed in diagnostic applications.

7 Claims, 23 Drawing Sheets

FIG. 2A

SB33 Hin47 sequence

```
GGATCCGTTAATACTGAAATAAATGGCACACCTTTTTCACGCATTTGGGCAAGTACAGCA
         10        20        30        40        50        60

CTGGTTTTTGCCATTTGCATTAAAGAGAATAATGCTTCCTGCATACGAGCACCACCACTC
         70        80        90       100       110       120

GCAGAGAAACATACAAAACGGACAATTCATTTCCATCGCTTTTTCAGCCGCTTTAACAAAT
        130       140       150       160       170       180

TTTGCACCAACTACAGAACCCATTGAACCGCCCATAAAAGCAAAGTTCGATGCAGCCACA
        190       200       210       220       230       240

ACAATTGGCATATCATAAAGTGTACCTGTCATAGTAATTAGCGCATCTTTCTCGCCCGTT
        250       260       270       280       290       300

TCTTTTTGTGCCGCATTGATACGATCTTTTATATTTCTTTAAATCTTTAAATTTTAAAATA
        310       320       330       340       350       360
```

FIG. 2B

```
TCTTTTGGTTCTAAATCTGCCGCAATTTCTTGGCTTGAATCTTCGTCCAATAAATTTAAT
        370         380         390         400         410         420

AAACGCTCACGAGCATCAATACGCATATGATGACCACATTTCGGGCAAACATACAGATTA
        430         440         450         460         470         480

CGTTTGAGTTCTTCACTATAAAGTACTTGTTCACAAGCAGTACATTTGTCCATACGCCT
        490         500         510         520         530         540

TCTGGCACATTGGCTTTTCGAGTGGGAAGAAGGACTTTTACTAAAAATTCGGTTAATC
        550         560         570         580         590         600

CAGCTCATTTTTTGACCTTTTTATTGACTAGAAAATTGCGCGTATTAGAACATAAATTTA
        610         620         630         640         650         660

TAGAATTTGCTACTTGTAAGACCGTTTTTGTACTGCTCCGATTTCCTTTTAAACAAGATA
        670         680         690         700         710         720

ATTTGCTCTCCTCTTATTGAACATTTTTTATTTTTGTCTTACTGACCACGTTATCT
        730         740         750         760         770         780
```

FIG. 2C

```
                                        met lys lys thr arg phe val leu asn ser ile ala leu
                                        MET LYS LYS THR ARG PHE VAL LEU ASN SER ILE ALA LEU
GAAATTTATTTTGGAGTATTTATGAAAAAACACGTTTGTACTAAATAGTATTGCACTT
                790                   800               810               820               830              840
                                                        atgaaaaacacgttttgtattaaatagtattgcactt gly leu ser val leu ser thr ser ser phe val ala gln ala thr leu pro ser phe val ser
GLY LEU SER VAL LEU SER THR SER SER PHE VAL ALA GLN ALA THR LEU PRO SER PHE VAL SER
GGATTAAGTGTATTAAGCACATCATTTGCTCAAGCCACTTTGCCAAGTTTTGTTTCG
               850                    860               870               880               890              900
g g glu gln asn ser leu ala pro met leu glu lys val gln pro ala val val thr leu ser
GLU GLN ASN SER LEU ALA PRO MET LEU GLU LYS VAL GLN PRO ALA VAL VAL THR LEU SER
GAACAAAACAGTCTTGCACCAATGTTAGAAAAGTACAACCTGCCGTTGTCACTCTTTCC
               910                    920               930               940               950              960 val glu gly lys ala lys val asp ser arg ser pro phe leu asp asp ile pro glu glu
VAL GLU GLY LYS ALA LYS VAL ASP SER ARG SER PRO PHE LEU ASP ASP ILE PRO GLU GLU
GTTGAAGGAAAAGCTAAAGTAGATTCTCGTTCTCCTTTCCTAGACGATATTCCTGAAGAA
               970                    980               990              1000             1010             1020 phe lys phe phe phe gly asp arg phe ala glu gln phe gly gly arg gly glu ser lys
PHE LYS PHE PHE PHE GLY ASP ARG PHE ALA GLU GLN PHE GLY GLY ARG GLY GLU SER LYS
TTTAAATTCTTCTTTGGCGATCGTTTTGCCGAACAATTTGGTGGACGTGGAGAATCAAAAG
              1030                    1040             1050             1060             1070             1080
```

FIG. 2D

```
ARG ASN PHE ARG GLY LEU GLY SER GLY VAL ILE ILE ASN ALA SER LYS GLY TYR VAL LEU
CGTAACTTCCGTGGTTTAGGTTCTGGTGTCATTATTAATGCAAGCAAAGGCTATGTTTTA
            1090                1100                1110                1120                1130                1140

THR ASN ASN HIS VAL ILE ASP GLU ALA LYS ILE THR VAL GLN LEU GLN ASP GLY ARG
ACCAATAATCATGTTATTGATGAAGCTGATAAAATTACCGTGCAATTACAAGATGGGCGT
            1150                1160                1170                1180                1190                1200

GLU PHE LYS ALA LYS LEU VAL GLY LYS ASP GLU LEU SER ASP ILE ALA LEU VAL GLN LEU
GAATTTAAAGCAAAATTAGTGGGTAAAGATGAACTATCAGATATTGCATTAGTACAGCTT
            1210                1220                1230                1240                1250                1260

GLU LYS PRO SER ASN LEU THR GLU ILE LYS PHE ALA ASP SER ASP LYS LEU ARG VAL GLY
GAAAAACCAAGTAATTTAACAGAAATCAAATTTGCTGATTCCGACAAATTACGCGTAGGC
            1270                1280                1290                1300                1310                1320

ASP PHE THR VAL ALA ILE GLY ASN PRO PHE GLY LEU GLY GLN THR VAL THR SER GLY ILE
GATTTCACTGTTGCAATCGGTAATCCATTTGGTTTAGGTCAAACTGTGACATCAGGTATT
            1330                1340                1350                1360                1370                1380

VAL SER ALA LEU GLY ARG SER THR GLY ARG SER ASP SER GLY THR TYR GLU ASN TYR ILE GLN
GTTTCTGCATTGGGTCGTTCAACAGGTTCTGACAGTGGCACTTATGAAAACTATATTCAA
            1390                1400                1410                1420                1430                1440

THR ASP ALA ALA VAL ASN ARG GLY ASN SER GLY GLY ALA LEU VAL ASN LEU ASN GLY GLU
ACCGATGCAGCAGTAAACCGCGGTAATTCGGGTGGAGCGTTAGTAAACTTAAATGGCGAA
            1450                1460                1470                1480                1490                1500
```

FIG. 2E

| LEU | ILE | GLY | ILE | ASN | THR | ALA | ILE | ILE | SER | PRO | SER | GLY | GLY | ASN | ALA | GLY | ILE | ALA | PHE |
|---|---|---|---|---|---|---|---|---|---|---|---|---|---|---|---|---|---|---|---|
CTTATTGGAATTAATACCGCAATTATTTCTTCCAAGCGGTGGCAATGCAGGAATTGCCTTT
1510          1520          1530          1540          1550          1560

| ALA | ILE | PRO | SER | ASN | GLN | ALA | SER | ASN | LEU | VAL | GLN | ILE | LEU | GLU | PHE | GLY | GLN | VAL |
|---|---|---|---|---|---|---|---|---|---|---|---|---|---|---|---|---|---|---|
GCGATTCCAAGTAATCAAGCAAGCAATTAGTGCAAATTTAGAATTTGGTCAAGTG
1570          1580          1590         1600         1610         1620

| ARG | ARG | GLY | LEU | LEU | GLY | ILE | LYS | GLY | ILE | GLY | LEU | ASN | ALA | ASP | LEU | ALA | LYS | ALA | PHE |
|---|---|---|---|---|---|---|---|---|---|---|---|---|---|---|---|---|---|---|---|
CGTCGCGGATTGCTTGGTATTAAAGGTATTGGCGAACTCAATGCTGATTTAGCCAAAGCCTTT
1630          1640          1650          1660          1670          1680

| ASN | VAL | SER | ALA | GLN | GLN | GLY | ALA | PHE | VAL | SER | GLU | VAL | LEU | PRO | LYS | SER | ALA | ALA | GLU |
|---|---|---|---|---|---|---|---|---|---|---|---|---|---|---|---|---|---|---|---|
AATGTAAGCGCGCAAGGCCATTTGTAAGTGAAGTTTACCGAAATCTGCTGAA
1690          1700          1710          1720          1730          1740

| LYS | ALA | GLY | LEU | LYS | ALA | GLY | ASP | ILE | ILE | THR | ALA | MET | ASN | GLY | GLN | LYS | ILE | SER | SER |
|---|---|---|---|---|---|---|---|---|---|---|---|---|---|---|---|---|---|---|---|
AAAGCAGGACTTAAAGCGGGCGATATTATCACGGCGATGAACGGTCAAAAATCTCAAGT
1750          1760          1770          1780          1790          1800

| PHE | ALA | GLU | ILE | ARG | ALA | LYS | ILE | ALA | THR | THR | GLY | ALA | GLY | LYS | GLU | ILE | SER | LEU | THR |
|---|---|---|---|---|---|---|---|---|---|---|---|---|---|---|---|---|---|---|---|
TTCGCTGAAATTCGTGCAAAATCGCAACCACTGGTGCAGGCAAAGAGATTAGCTTGACT
1810          1820          1830          1840          1850          1860

FIG. 2F

```
TYR LEU ARG ASP GLY LYS SER HIS ASP VAL LYS MET LYS LEU GLN ALA ASP ASP SER SER
TACTTACGTGATGGCAAATCCCACGACGTTAAAATGAAATTACAAGCGGATGATAGTAGC
        1870            1880           1890          1900           1910           1920

GLN LEU SER SER LYS THR GLU LEU PRO ALA LEU ASP GLY ALA THR LEU LYS ASP TYR ASP
CAACTTTCCTCAAAAACTGAGTTGCCCTGCATTAGATGGTGCAACATTGAAAGACTACGAT
        1930           1940           1950           1960           1970           1980

ALA LYS GLY VAL LYS SER GLY ILE ILE GLU THR LYS ILE GLN PRO ASN SER LEU ALA ALA GLN
GCTAAAGGCGTTAAATCGGGAATTGAAAGGAATCACAAAAATTCAACCTAATTCGCTGGCACAA
        1990           2000           2010           2020           2030           2040

ARG GLY LEU LYS SER GLY ASP ILE ILE ILE GLY ILE ILE ASN ARG GLN MET ILE GLU ASN ILE
CGTGGTTTAAAATCGGGCGATATTATTGGTATTAATCGTCAAATGATCGAAAACATT
        2050           2060           2070           2080           2090           2100

ARG GLU LEU ASN LYS VAL LEU GLU THR GLU PRO SER ALA VAL ALA LEU ASN ILE LEU ARG
CGTGAATTAAATAAAGTGCTTGAAACTGAACCCGTCAGCAGTTGCACTTAATATTTACGA
        2110           2120           2130           2140           2150           2160

GLY ASP SER ASN PHE TYR LEU LEU VAL GLN ***
GGTGACAGTAATTTCTATTTATTAGTGCAATAATCTGCTTGATATATTTAAGAAAAAAGT
        2170           2180           2190           2200           2210           2220
```

FIG. 2G

```
CCGATCACACAATGATCGGGCTTCTTTTTATGCAGCAATCGTTCTTAACAAATCCACCACAA
2230                2240                2250                2260                2270                2280

ATTCTAACCGCACTTTGTTATCAGATAAATCTTTCATGAACTTAAATTTTAATGGGCCAT
2290                2300                2310                2320                2330                2340

CAAATCGATACACAATAGGTTCTTTTTGAATTAATTGAATAAATTTATCTGGATTCACTT
2350                2360                2370                2380                2390                2400

GTGCTTTTGCTGAAAACTCAATAAAACCGCCTTGTGTTCCCTGCATCAATTCGCACAACTT
2410                2420                2430                2440                2450                2460

TCAACGGCTCAACCAACAAACGCAATTCTGCAATTTGCAGTAAAATTTTTTGTTGCATCAG
2470                2480                2490                2500                2510                2520

GCAATAATCCGAATCGATCTATTAACTCAACTTTTAATTCATCTAATTCTGCTTTACTCT
2530                2540                2550                2560                2570                2580

CTGCTGCAGCAATGCGTTTATAAAAGGATAAACGCATATTCACGTCTCCTAGATAATCAT
2590                2600                2610                2620                2630                2640
```

FIG.2H

```
CAGGCAGTAAAGCAGGCACACGCAATTCAATATCCGCTTGTTGCGTCAATTCTTCTA
2650                2660              2670              2680              2690              2700

ATGATGGTTCACGCCCTTCTTTTAACGCTTTAACCGCTGCATCCAATAATTCCATATAAA
2710              2720              2730              2740              2750              2760

GCGAAAACCGATGCTTTCAATTTGTCCACTTTGTTTCGTTTCCAAGTAATTCGCCGGCAC
2770              2780              2790              2800              2810              2820

CACGAATCTCTAAATCGTGGGTTGCCAAGATAAAACCAGCCCCAAGATTATCAAGATTTT
2830              2840              2850              2860              2870              2880

CCAACGCATCTAGA
2890
```

FIG. 3A

Comparison of Hin47 with E.coli htrA and S.typhimurium htrA

```
MKKTIRFVLNSIAIGLS---VLS-TSFVAQATLPSFVSEQ--NSLAPMLEKVQP            Hin47
....TLA.SRL..S..-LA..PL.AT.AE.-S.ATTA.QMP.........M.              E. coli
--T.AMS..A..IGLA..PL.AT.AE.SS.AMTA.QMP.........M.                 S. typh AVVTLSVEGKAKV-DSRSP------FLDDIP--EEFKFFGDRF--A         Hin47
             S..SIN...STT.NTP.M.RNFQQF.G..S.FCQ.GSP.QSSP.CQG        E. coli
             S..SIN...STT.NTP.M.RNFQQF.G..S.FCQDGSP.QNSP.CQG        S. typh EQFGGRGESKRNFRGIGSSGVIINASKGYVLINNHVIDEADKITVQLQDGREFK            Hin47
G.G.NG.GQQK.MA.......D.D....V......V.N.TV.K...S...K.D            E. coli
GGN.GN.GQQK.MA.......D.A....V......V.N.SV.K...S...K.D            S. typh AKLVGKDELSDIALVQLEKPSNLIEIKFADSDKLRVGDFTVAIGNPF         Hin47
             ..M.....PR.....I.IQN.K..A.M...A....Y.G.....           E. coli
             ...V.....PR.....I.IQN.K..A.L...A.....Y.........       S. typh GLGQIVISGIVSALGRSIGSDSGIYENYIQTDAAVNRGNSGGALVNINGELIG             Hin47
...E...........- .INAEN...F.....I............                    E. coli
...E...........- .INVEN...F.....I............                    S. typh
```

FIG. 3B

```
INTATISPSGGNAGTAFATPSNQASNLVQQILEFGQVRRGLLGIKGG    Hin47
.....LA.D...I.G......MK..TS.MV.Y...K..E...M.T     E. coli
.....LA.D...I.G......MK..TS.MV.Y......E...M.T     S. typh EINADLAKAFNVSAQQGAFVSEVLPKSAAEKAGLKAGDIITAMNQKISSFAE
....SE.....MK.D..R.....Q...N.S.A...I....V..SL..KP.....A
....SE.....MK.D..R.....Q.M.N.S.A...I....V..SL..KP.....A IRAKIATIGAGKEISLTYLRDGKSHDVKMKLQADDSSQLSSKIELPA    Hin47
L..QVG.MPV.SKLT.GL.....QVN.NLE..QSSQN.VD.SSIFNG    E. coli
L..QVG.MPV.SK...GL..E..AIT.NLE..QSSQ..VD.S.IFSG    S. typh LDGA--TLKDYDAKGVKGIETIKIQPNSLAAQRGIKSGDIIIGINRQMIENIR
IE..EMSN.GK.QGV.VNNVK.----GTP...I...K..V...A.Q.AVK..A
IE..EMSN.GQ.KGV.VSSVKA----...P...I...K..V...A.Q.PVK..A EINKVLETEPSAVALNIILRGDSNFYLLVQ*                    Hin47
..R...DSK..VL.....Q....--RH.P.N*                   E. coli
..R.I.DSK..VL.....Q.....SI....M.*                  S. typh
```

FIG. 4A

| | | | |
|---|---|---|---|
| TON  : | IVGGYKCEKNSQPWQVAVIN | ------E---YLCGG | VLID |
| PKAAB: | IIGGCEKNSHPWQVAIYHY | ------SS--FQCGG | VLVN |
| PIN  : | IVGGYTCGANTVPYQVSLN | ------SGY-HFCGG | SLIN |
| CHAA : | IVNGEEAVPGSMPWQVSLQDK | ---TGF----HFCGG | SLIN |
| EST  : | VVGGTEAQRNSWPSQISLQYRSGSSWA | ---HTCGG | TLIR |
| RP2A : | IIGGVESIPHSRPYMAHLDIV | ---TEKGLRVICGG | FLIS |
| SGT  : | VVGGTRAAQGEFPFMVRLSM | ------GCG | ALYA |
| SGBE : | ISGG | ---DAIYSS | ---TGRCSLGFNVRSGS |
| SGA  : | IAGG | ---EAITIG | ---GSRCSLGFNVSVNG |
| ALP  : | ANIVGG | ---IEYSIN | ---NASLCSVGFSVTRGA |
| hin47: | AEQFGG | RGESKR | N FRGLGSGVIINAS |
| | ****** | | ** |
| ccn | <----> | <-------> | <------> |

| | |
|---|---|
| | # (His57) |
| TON  : | ------PSWVITAAHCY---S---N-NYQ-VLLGRNNLFK-DEPFAQRRLV |
| PKAAB: | ------PKWVLTAAHCK---N-----DNYEV-WL-GRHNLFENENT-AQFFGV |
| PIN  : | ------SQWVVSAAHCY---X-----SGIQV-RL-GEDNINVEGN-EQFISA |
| CHAA : | ------ENWVVTAAHCG---V------TTSDV-VVAGEFDQGSSSEK-IQKLKI |
| EST  : | ------QNWMMTAAHCV---D------RELITFRVVGEHNLNQNGT-EQYVGV |
| RP2A : | ------RQFVLTAAHCK------GREIT-VILGAHDVRKREST-QQKIKV |
| SGT  : | ------QDIVLTAAHCV---SGSGNNTSIT-ATGGVVDL-QSG-A-AVKVRS |

FIG. 4B

```
SGBE  :                          TYYFLTAGHCT--D-------GATT-WWA---------NS-ARITVL
SGA   :                          VAHALTAGHCT---------------NISASW----------SI
ALP   :                          TKGFVTAGHCGIVN---------AT-AR-IG----------GAVVG
Sal.T :                          KGYVVINNHVVDNASVIKVQLSDGR
hin47 :                          KGYVLINNHVIDEA          DK-IT-VQ--------LQDGRE
                                 ********
ccn           <------------------->        <------X------->        <--->

# (Asp102)
TQN    : RQS-FRHPDYIPLI PVHDH---SNDIMLHISEPADITGGVKV------------
PKAAB  : TAD-FPHPGFNLSAD-GKDY---SHDIMLRLQSPAKITDAVKV------------
PIN    : SKS-IVHPSYN--------SNIL---NNDIMLKLKSAASLNSRVAS---------
CHAA   : AKV-FKNSKYN--------SLITI--NNDTTLIKLSTAASFSQTVSA--------
EST    : QKI-VVHPYWN--------TDDVAAGYDIALIRLAQSVTLNSYVQL---------
RP2A   : EKQ-IIHESYN--------SVPN---LHDIMLIKLEKKVELTPAVNV--------
SGT    : TKV-LQAPGYN--------G-T---GKDWALIKLAQPIN------QPT-------
SGBE   : GTT-SGS-SF---------PNNDYGIVRYINTTPX   DGTVG-----------
SGA    : GTR-TGT-SF---------PNNDYGIIRHSNPAAA         DGRVYLYNGS---
ALP    : -TFAARV-F----------PGNDRAWSLTSAQTL-----LPRVANGSS------
hin47  :    FKAKLVG         KDEL   SDIALVQLEKPSNL    TEIKFADSDKLRVGDF
                                  ********* ccn    <---X----->      <-X->         <--------X------>     <--->
```

FIG. 4C

| | | | |
|---|---|---|---|
| TON : | ---IDLPT--KEPKVGSICLASGMGSINPS-E-MVVSHDLQCVNIHLLSN | | EKCIE--TYKIDNVT-DMLCA-G-E---MEGGK-DICA--GDSGGPLIC- |
| PKAAB: | ---LELPT-QEPE-LGSICEASGMGSIEPGPDDFEFPDEIQCVQLTLQN | | TFCAD--AHPDKVT-ESMLCAGY-L---P--GGKDTCM--GDSGGPLIC- |
| PIN : | ----ISLPT-SCAS-AGTQCLISGMGNIKSS--GISYPDVLKCLKAPILSD | | SSCKS--AYPGQIT-SMFCAGY-L---E--GGKDSCQ--GDSGGPWC- |
| CHAA : | ----VCLPSASDFAAGTICVITIGMLTRY---:--ANTPDRLQQASLPLLSN | | TNCKK--YWGTKIK-DAMICA-G-A---S--GV-SSQM--GDSGGPLVC- |
| EST : | ----GVLPRAGTLLANSPCYTTIGMGLTR-T---NGQLAQTLQQAYLPTVDY | | AICSSSSYWGSIVK-NSMVCA-G-G---D--GVRSGCQ--GDSGGPLHC- |
| RP2A : | ----VPLPSPSDFTHPGAMCVVAAGMGKTGVR---DPT-SYTLREVELRIMDE | | KACVDYRYEYKF----QVCV-GSP---T--TLRAAFM--GDSGGPLIC- |
| SGT : | ---LKIAT--TTAYNQGTFTVAGMGANRE----GGSQQRYLLKANVPFVSD | | AACRS--AYGNELVANEEICA-G-YPDTG--GV-DTCQ--GDSGGMFR- |
| SGBE : | GQDITSAA NATVGMAVTRRGSTT----------GIHSGSVTAL | | NATVN--YGGGDVV-YGMIRT-N------------VCAEPGDSGGPLYS- |
| SGA : | YQDITTAG NAFVGQAVQRSGSTT----------GLRSGSVIGL | | |
| ALP : | FVTVRGST--- EAAVGAAVCRSGRIT----------GYQCGTITAK | | |
| hin47: | TVAIGNPFGLGQTVISGIVSALGRST GSDSGTYENY | | |
| | ******* ** | | | con : -------> <--|--> <----> # (Ser195)

FIG. 4D

```
SGA    : NATVN--YGSSGIV-YGMIQT-N-----------------VCAQPDGSGSLFA-
ALP    : NVTAN--Y-AEGAV-RGLTG-N-A-----------CMGR--GDSGGSWITS
hin47  :                                    AVNR  GNSGGALVNLN
                  *** * *          IQT D A    ****   *******
con              <------>         <---->           <-X------>

TGN    : D-------GVLQGITSGGA-TP------C-A-KP--K-T-PAIYAKLIKFT-SW
PKAAB  : NG------MWQGITSMGH-TP------C-GSA---N-K-PSIYKLIFYL-DW
PIN    : SGK------LQGIVSMGS--G------C-AQK---N-K-PGVYIKVCNYV-SW
CHAA   : KKN-GAWILVGIVSMGS-ST------C-S-T---S-T-PGVYARVTALV-NW
EST    : LVN-GQYAVHGVISFVSRLG-------C-NVT---R-K-PIVFIRVSAYI-SW
RP2A   : --A-GV---AHGIVSYG----------HPD---A-KPPAIFIRVSTYV-PW
SGT    : KDNADEMIQVGIVSMGY--G------C-A-R---PGY-PGVYTEVSIFA-SA
SGBE   : G-------TRAIGLTSGGS-GN-----C-S-S---G-G-TIFFQPVTEALVAY
SGA    : G-------STAIGLTSGGS-GN-----C-R-T---G-G-TIFYQPVTEALSAY
ALP    : A-------GQAQGVMSGGN-VQSNGNCG-IPASQ-R--SSLFERLQPIL-SQ
hin47  : GELIGINIAII SP SGGNAG IAFAI P SNQASNLVQQLL
                                ????
con    >----------------------->           <-X------->
```

FIG. 4E

```
TON    : IKKVMKENP
PKAAB  : IDDITENP
PIN    : IKQTIASN
CHAA   : VQQTLAAN
EST    : INNVIASN
RP2A   : INAVIN
SGT    : IASAARIL
SGBE   : GVSVY
SGA    : GAIVL
ALP    : YGLSLVIG
hin47  : EFGQVRRGLLGIKG
con          ------->
```

Digestion of β-Casein by Hin47

1. β-Casein + Hin47
2. β-Casein + Mutant
3. β-Casein

A. Each lane contains 5μg of β-casein, +/- 20 ng of Hin47 or mutant
B. Each lane contains 5μg of β-casein, +/-0.1 μg of Hin47 or mutant
C. Immuno-blot with rabbit anti-Hin47 antibody

IMMUNO-BLOT ANALYSIS ON THE STABILITIES OF HIN47 AND MUTANT

Day 0   Day 10   Day 20

H: Hin47    1. -20°C
M: Mutant   2. 4°C

ANALOG OF HAEMOPHILUS HIN47 WITH REDUCED PROTEASE ACTIVITY

REFERENCE TO RELATED APPLICATIONS

This application is a division of U.S. patent application Ser. No. 08/482,816, filed Jun. 7, 1995, which is a continuation-in-part of U.S. patent application Ser. No. 08/278,091 filed Jul. 21, 1994, now U.S. Pat. No. 5,506,139.

FIELD OF THE INVENTION

The present invention relates to the field of immunology and is particularly concerned with immunogens and antigens from species of Haemophilus.

BACKGROUND TO THE INVENTION

Haemophilus influenzae is the organism responsible for a variety of serious human diseases, such as meningitis, epiglotitis, pneumonia and otitis media. Haemophilus influenzae type b (Hib) is a major cause of bacterial meningitis in children under the age of five years. Protective antibodies to the disease are induced by the capsular polysaccharide of the organism and vaccines have been developed that utilise the purified polyribosyl ribitol phosphate (PRP) as the antigen. This vaccine provides 90% protection in adults and in children over 24 months of age, but was ineffective in children under 24 months (Zangwill et al 1993). (The references are identified in a list of references at the end of this disclosure, each of which reference in the list is hereby incorporated by reference without further reference thereto). Like other polysaccharide antigens, PRP does not induce the proliferation of T-helper cells, and re-immunisation fails to elicit either a booster response or an increase in memory cells. Conjugation of the PRP polysaccharide with protein carriers confers T-cell dependent characteristics to the vaccine and substantially enhances the immunologic response to the PRP antigen. Currently, there are four PRP-carrier conjugate vaccines available. These are vaccines based upon H. influenzae type b capsular polysaccharide conjugated to diphtheria toxoid, tetanus toxoid, or Neisseria meningitidis outer membrane protein (reviewed in Zangwill et al, 1993). These H. influenzae b conjugate vaccines have dramatically reduced the incidence of bacterial meningitis (Schoendorf et al, 1994).

There are six serotypes of H. influenzae designated a to f, which are defined by their capsular polysaccharides. The current Haemophilus conjugate vaccines do not protect against other invasive typable strains (types a and c) and, importantly, do not protect against non-typable (NTHi) strains which are a common cause of postpartum and neonatal sepsis, pneumonia and otitis media. Otitis media is the most common illness of early childhood with approximately 70% of all children suffering at least one bout of otitis media before the age of seven. Chronic otitis media can lead to hearing, speech, and cognitive impairment in children. It is caused by bacterial infection with Streptococcus pneumoniae (approximately 50%), non-typable H. influenzae (approximately 30%), and Moraxella (Branhamella) catarrhalis (approximately 20%). In the United States alone, treatment of otitis media costs between 1 and 2 billion dollars per year for antibiotics and surgical procedures, such as tonsillectomies, adenoidectomies and insertion of tympanostomy tubes. To achieve universal protection against H. influenzae related diseases, particularly in the two to six month age group and certain high risk groups, the provision of conserved, cross-reactive non-capsular H. influenzae immunogens is desirable. Non-typable strains of H. influenzae are also important pathogens responsible for pneumonia in the elderly and other individuals who are particularly susceptible to respiratory infections. There is thus a need for antigens from H. influenzae which are useful as components in immunogenic preparations that provide protection against the many serotypes of H. influenzae. PCT application WO 92/10936, published Jul. 9, 1992 and incorporated herein by reference thereto, describes a 47,000 molecular weight outer membrane protein obtained from H. influenzae that is reported to be an adhesin and has been termed Hin47 that is immunologically conserved between non-typable, type b and non-typed clinical isolates of H. influenzae. The amino acid sequence of Hin47 and the nucleotide sequence of the gene encoding Hin47 were presented at the American Society of Microbiology (ASM) conference held in New Orleans, May 26–30, 1992. These sequences have also been published in PCT application WO 94/00149, published Jan. 6, 1994 and incorporated herein by reference thereto.

Since Hin47 is conserved among strains of Haemophilus influenzae, and is reported to be an adhesin, the protein has utility in diagnosis of and vaccination against disease caused by H. influenzae or other bacterial pathogens that produce Hin47 or a protein capable of raising antibodies specifically reactive with Hin47.

A disadvantage of Hin47 for use as an antigen in diagnosis, for the generation of anti-Hin47 antibodies useful in diagnosis and as an immunogen in vaccination is the unexpected discovery by the present applicants that Hin47 has protease activity which results in the autodigestion of Hin47 and the proteolytic degradation of other antigens mixed therewith.

It would be advantageous to provide analogs of Hin47 protein (sometimes referred to herein as mutants or derivatives) that are substantially reduced in proteolytic activity for use as antigens, immunogenic preparations including vaccines, carriers for other immunogens and the generation of diagnostic reagents.

SUMMARY OF THE INVENTION

The present invention is directed towards the provision of analogs of Haemophilus Hin47 protein having reduced protease activity.

In accordance with one aspect of the invention there is provided an isolated and purified analog of Haemophilus influenzae Hin47 protein having a decreased protease activity which is less than about 10% of natural Hin47 protein. Such Hin47 analog preferably has substantially the same immunogenic properties of natural Hin47 protein. The analog of the present invention may be produced by chemical, biochemical or genetic modification of natural Hin47.

In one embodiment of the present invention, when the analog is produced by genetic modification, at least one amino acid of the natural Hin47 contributing to protease activity may be deleted or replaced by a different amino acid to produce the reduced protease activity. Alternatively, the reduced protease activity may be achieved by inserting at least one amino acid into the natural Hin47 protein. The at least one deleted or replaced amino acid may be selected from amino acids 195 to 201 of Hin47, and specifically may be Serine-197, which may be deleted or replaced by alanine. In addition, the at least one deleted or replaced amino acid may be His-91 and may be deleted or replaced by alanine or lysine or arginine. Further, the at least one deleted or replaced amino acid may be Asp-121 and may be deleted or replaced by alanine or glutamic acid.

Figure 5A:
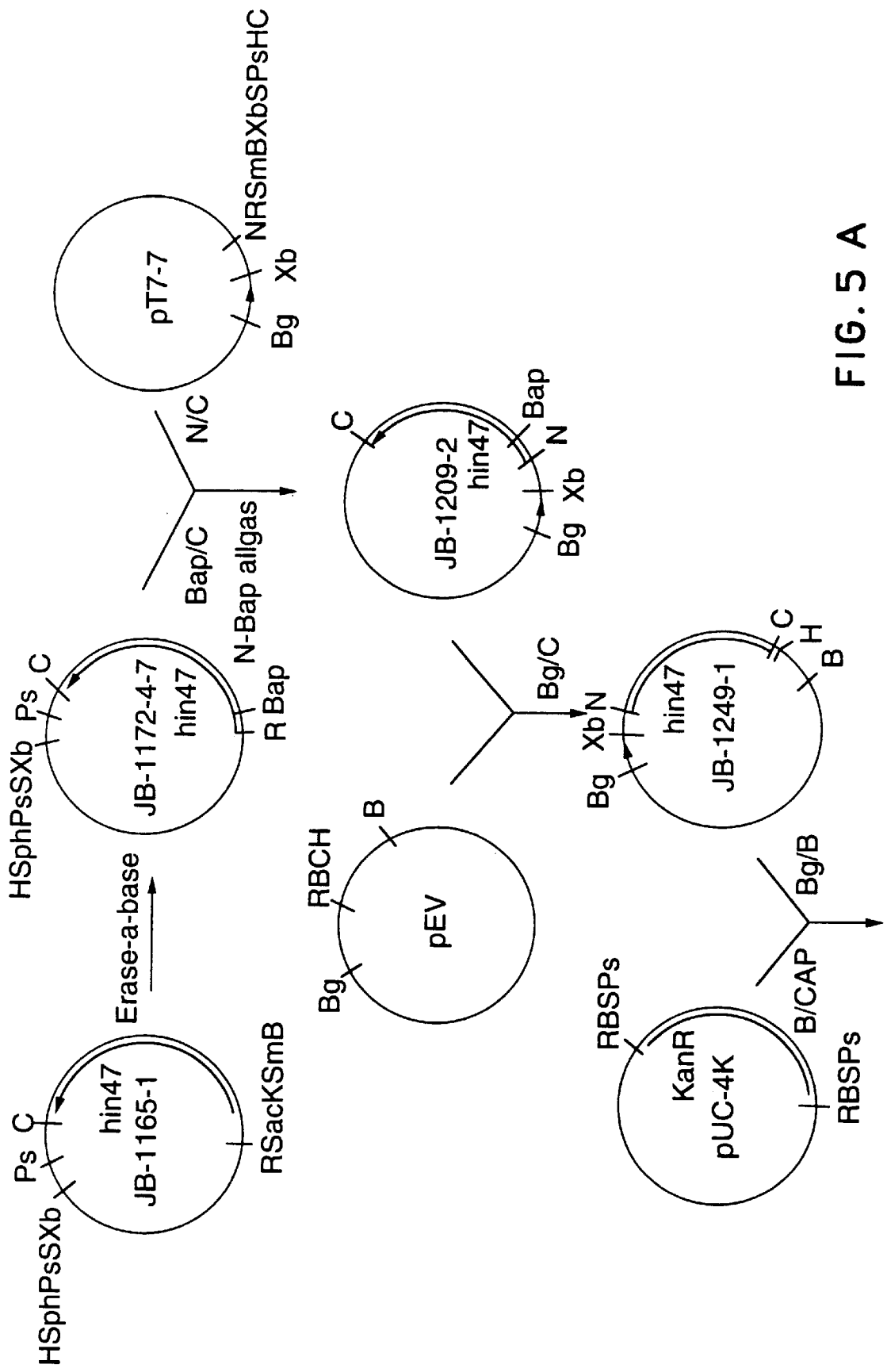
Figure 5B:
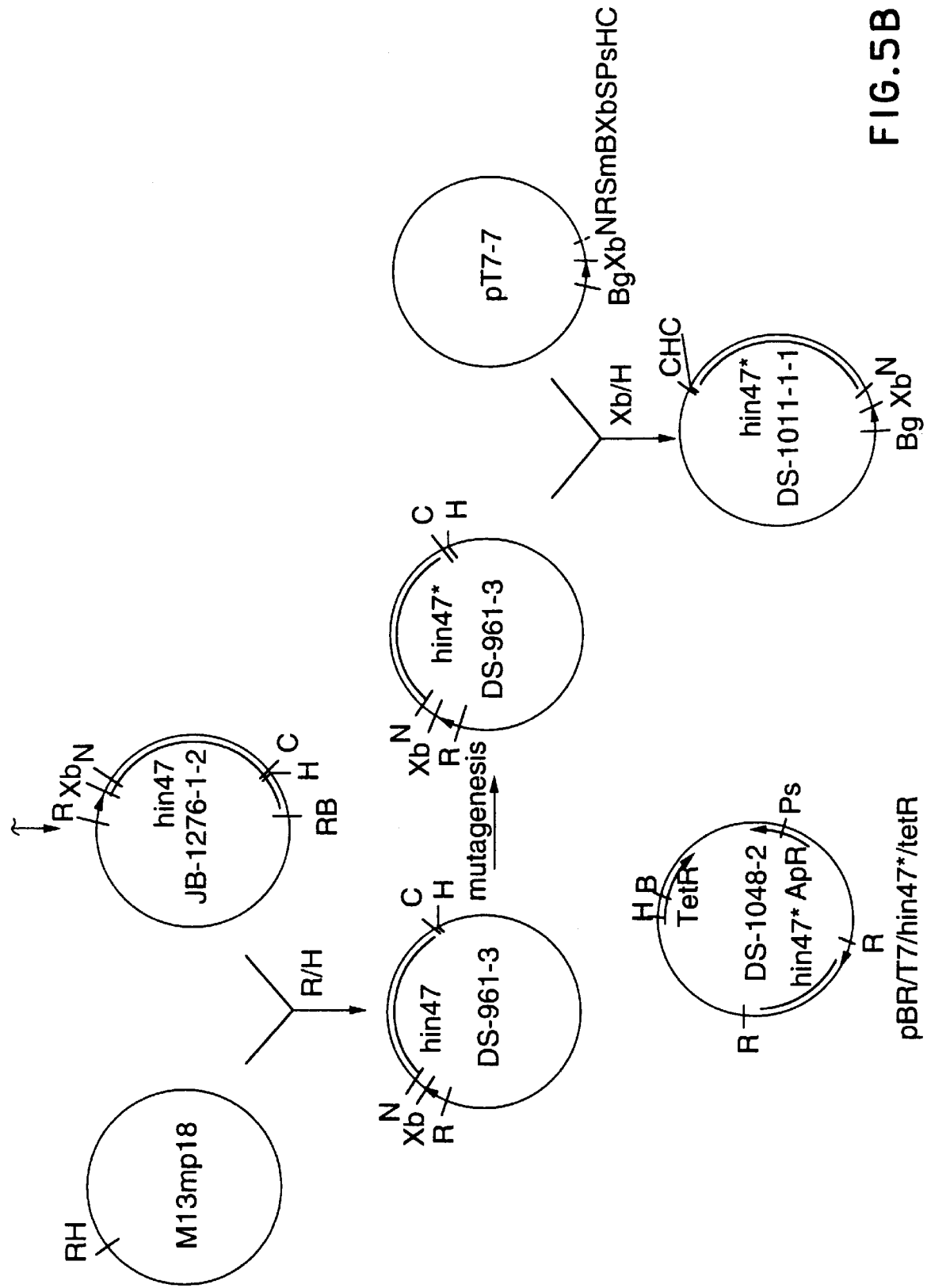
Figure 6:
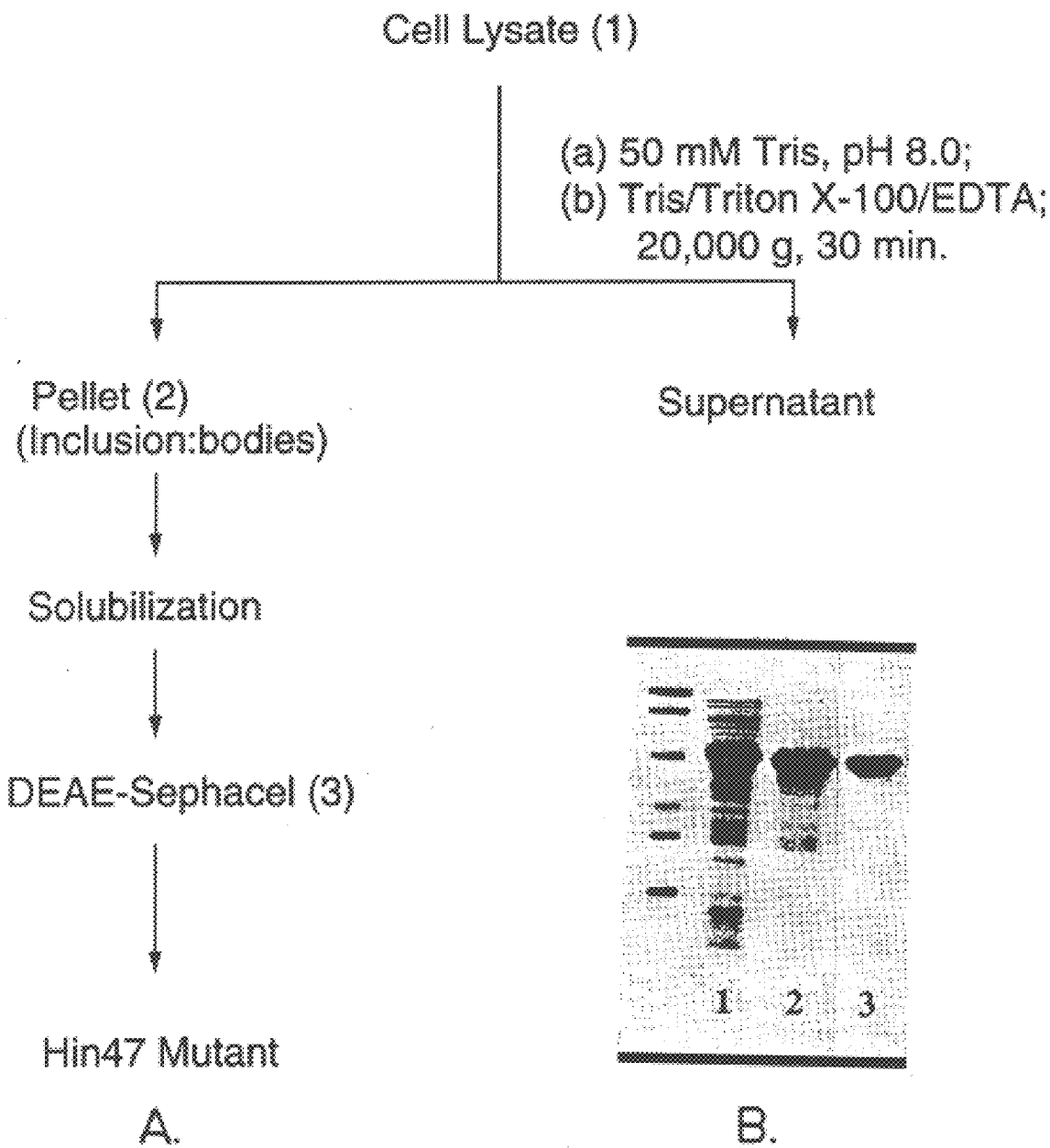
Figure 7:
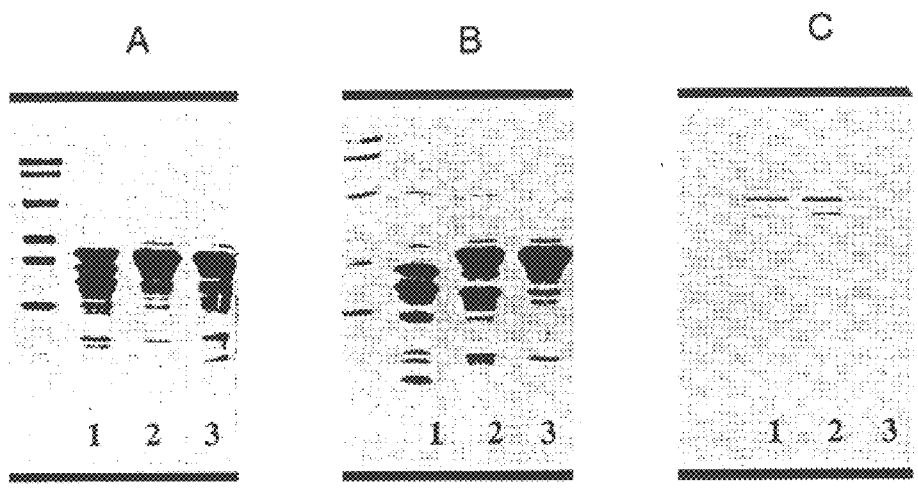
Figure 8:
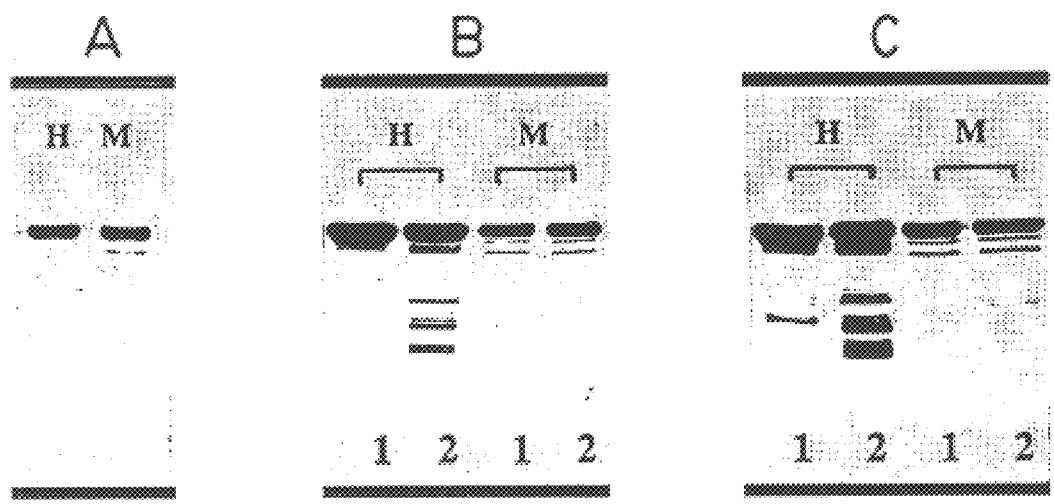
Figure 9:
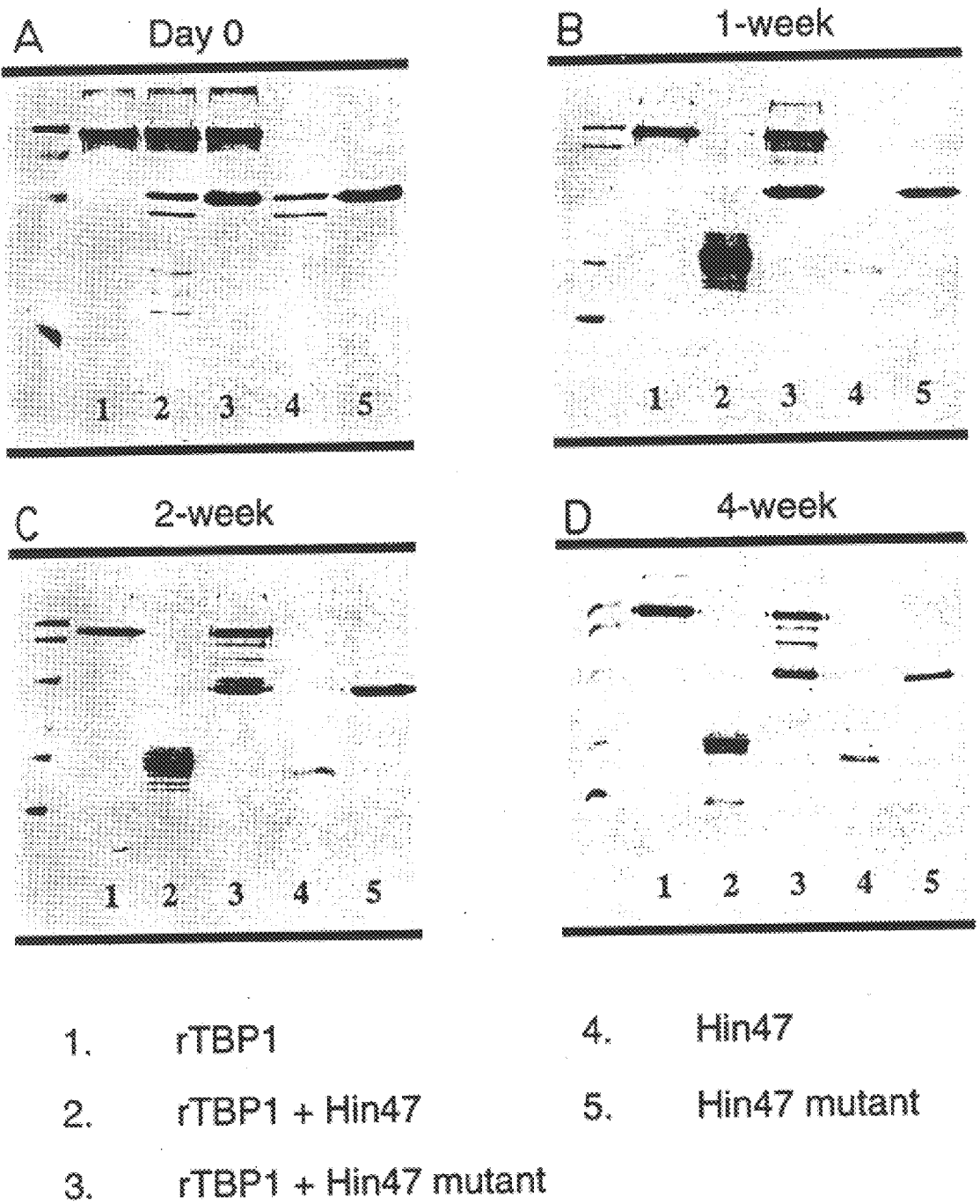
Figure 10:
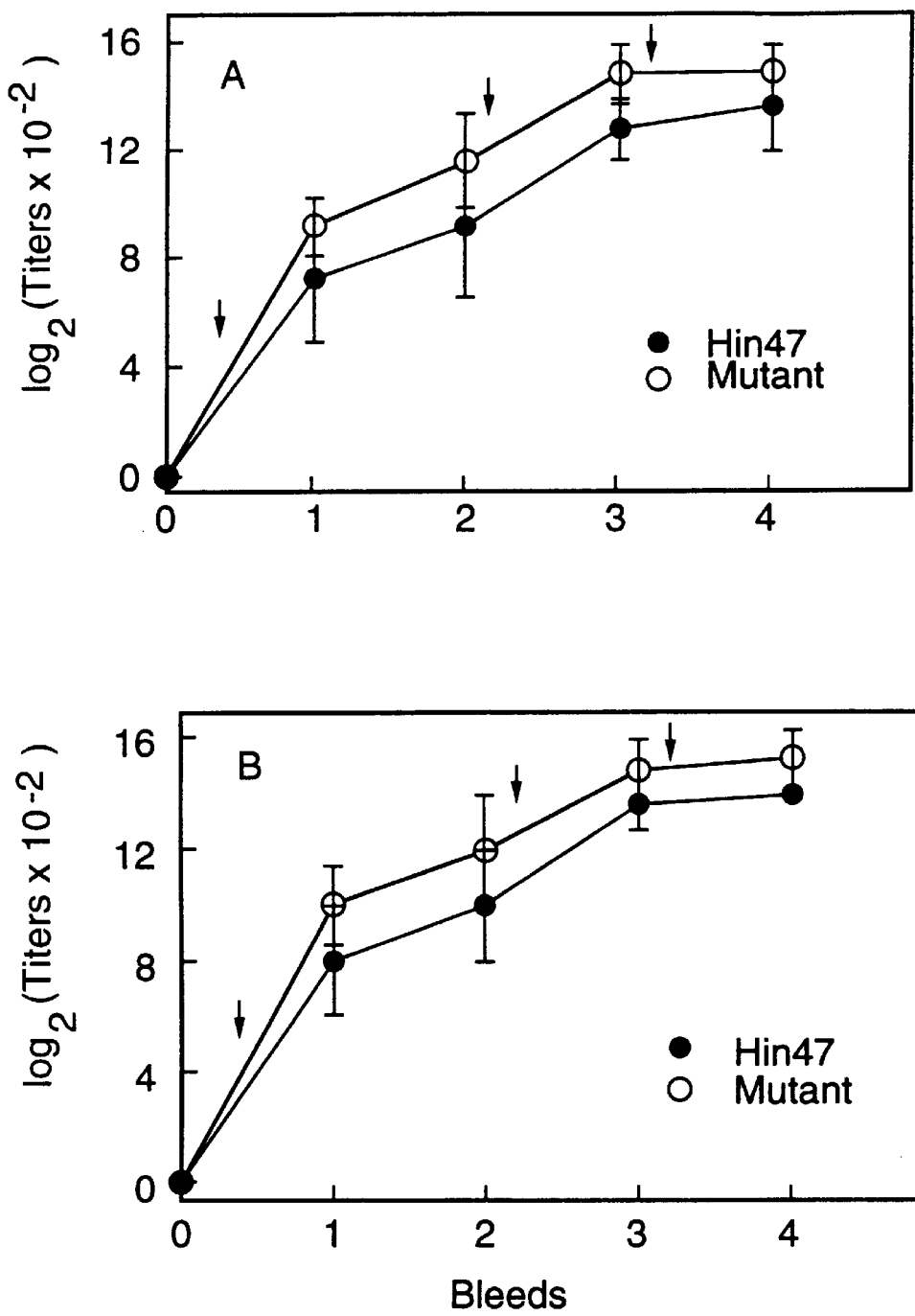

In a further aspect, the present invention provides an isolated and purified nucleic acid molecule comprising a mutant *Haemophilus influenzae* hin47 gene encoding an analog of *Haemophilus influenzae* Hin47 protein having a reduced protease activity which is less than about 10% of natural Hin47 protein. The mutant hin47 gene may encode any of the Hin47 analogs discussed above. The mutant gene preferably is formed by site-directed mutagenesis of a wild-type hin47 gene. The nucleic acid molecule may be contained in a recombinant plasmid adapted for transformation of a host and may be plasmid DS-1011-1-1 (deposited on Jul. 27, 1994 at American type Culture Collection under Accession No. 75845. The invention also includes a transformed cell containing such a recombinant plasmid.

The present invention, in another aspect, includes a method for producing an analog of *Haemophilus influenzae* Hin47 protein having a reduced protease activity which is less than about 10% of natural Hin47 protein, which comprises identifying at least one amino acid residue of Hin47 protein which contributes to protease activity thereof, effecting site-directed mutagenesis of the hin47 gene to remove or replace a nucleotide sequence encoding the at least one amino acid and to produce a mutated hin47 gene, introducing the mutated hin47 gene into a cell to produce a transformed cell and growing the transformed cell to produce the Hin47 analog. The at least one amino acid which is selected may be any of the ones specifically identified above with respect to the Hin47 analog.

The introduction of the mutated hin47 gene preferably produces a transformed cell in which the mutated hin47 gene is under control of the T7 promoter and the growing of the transformed cell and expression of the Hin47 analog by the T7 promoter then preferably is effected by culturing in an inducing concentration of lactose. Preferably, the introduction of the mutated hin47 is effected by transforming the cell with the recombinant plasmid DS-1011-1-1, sometimes otherwise referred to as plasmid pT7/Hin47*.

A further aspect of the invention provides a method of providing isolated and purified Hin47 analog, which comprises effecting the procedure described above for the production of the Hin47 analog to produce grown transformed cells harbouring inclusion bodies containing the Hin47 analog, disrupting the grown transformed cells to produce supernatant and the inclusion bodies, solubilizing the inclusion bodies to produce a solution containing Hin47 analog, chromatographically purifying the Hin47 analog from the solution free from cell debris, and isolating the purified Hin47 analog.

The analogs of Hin47 provided herein with their decreased proteolytic activity are useful as antigens in immunogenic composition, carriers for other immunogens, diagnostic agents and in the generation of diagnostic agents. The nucleic acid molecules also are useful as probes for diagnostic use and also as in immunogenic compositions.

In a further aspect of the invention, there is provided an immunogenic composition comprising an immuno-effective amount of the Hin47 analog or of the nucleic acid molecule including the gene encoding the Hin47 analog. The immunogenic composition may be formulated as a vaccine for in vivo administration to a host, including a human, to confer protection against diseases caused by a bacterial pathogen that produces Hin47 or a protein capable of inducing antibodies in the host specifically reactive with Hin47. The bacterial pathogen may be a Haemophilus species, such as *Haemophilus influenzae*. The immunogenic compositions of the invention may further comprise at least one other immunogenic or immunostimulating material, such as an adjuvant. In an additional embodiment, the nucleic acid molecule comprising a gene encoding the Hin47 analog may be contained within a live vector, such as a pox virus, Salmonella, poliovirus, adenovirus, vaccinia or BCG.

The invention also extends to a method of generating an immune response in a host, including a human, comprising administering thereto an immuno-effective amount of the immunogenic compositions provided herein.

As mentioned above, the Hin47 analog provided herein is useful in diagnostic applications. Accordingly, in an additional aspect of the invention, there is provided a method of determining the presence of antibodies specifically reactive with Hin47 in a sample, comprising the steps of:

(a) contacting the sample with the Hin47 analog having substantially the same immunogenic properties as the natural Hin47 protein as provided herein to produce complexes comprising the Hin47 analog and any such antibodies present in the sample specifically reactive therewith; and (b) determining production of the complexes.

The present invention also provides a method of determining the presence of Hin47 in a sample, comprising the steps of:

(a) immunizing a subject with an immunogenic composition as provided herein to produce antibodies specific for Hin47 protein;

(b) contacting the sample with the antibodies to produce complexes comprising any Hin47 present in the sample and the Hin47 specific antibodies; and (c) determining production of the complexes.

The invention also extends to a diagnostic kit for determining the presence of antibodies in a sample specifically reactive with Hin47, comprising:

(a) the Hin47 analog having substantially the same immunogenic properties as the natural Hin47 protein as provided herein;

(b) means for contacting the analog with the sample to produce a complex comprising the analog and any such antibodies present in the sample; and (c) means for determining production of the complex.

BRIEF DESCRIPTION OF THE DRAWINGS

FIG. 1 shows the restriction maps of plasmids JB-1031-1-14 and JB-1068-2-2 and the construction of the plasmids for sequence analysis;

FIGS. 2A, 2B, 2C, 2D, 2E, 2F, 2G and 2H show the full nucleotide (SEQ ID NO: 1) and deduced amino acid sequence (SEQ ID NO: 2) of Hin47 from *H. influenzae* strain SB33 as well as a partial nucleotide sequence (SEQ ID NO: 3) and a partial deduced amino acid sequence (SEQ ID NO: 4) thereof, the latter being specifically copied by an inventor herein from materials presented in the ASM conference as described above;

FIGS. 3A and 3B show a comparison of the amino acid sequences of *H. influenzae* Hin47 (SEQ ID NO:2), *E. coli* htrA (SEQ ID NO: 5), and *Salmonella typhimurium* htrA (SEQ ID NO:6);

FIGS. 4A, 4B, 4C, 4D and 4E show an alignment of amino acid residues 57 to 256 of Hin47 with certain known proteases (SEQ ID NOS: 7 to 16). Codes are as follows: TON, rat tonin; PKAAB, kallikrein; PTN, trypsin; CHAA, chymotrypsin; EST, elastase: RP2A, rat mast cell protease; SGT, Streptomyces griseus trypsin; SGBE, S.griseus proteinase A; SGA, S.griseus proteinase B; ALP, L.enzymogenes alpha-lytic protease; hin47, res. 57-256 of Hin47. Asterisks(*) denote structurally conserved regions. The catalytic triad residues are indicated by a hash mark (#). 'con' refers to regions of structural concensus, among the mammalian proteases;

FIGS. 5A and 5B show the restriction maps for plasmids DS-1011-1-1 and DS-1048-2 which express a Hin47 analog from E. coli and a construction scheme for plasmid DS-1011-1-1 (plasmid pT7/Hin47*);

FIG. 6, comprising panels A and B, shows a process for purifying the Hin47 analog from E. coli according to one embodiment of the present invention (Panel A) and gel analysis Panel B) of the purified product;

FIG. 7, comprising panels A, B and C, shows the protease activities of natural Hin47 and Hin47 analog towards β-casein;

FIG. 8, comprising panels A, B and C, shows the stability of natural Hin47 and the Hin47 analog at different temperatures;

FIG. 9, comprising panels A, B and C, shows the enzymatic degradation of an H. influenzae recombinant protein by natural Hin47 and the Hin47 analog; and FIG. 10, comprising panels A and B, shows the comparative immunogenicity of natural Hin47 and the Hin47 analog in mice.

GENERAL DESCRIPTION OF INVENTION

Any Haemophilus strains that have Hin47 genes may be conveniently used to provide the purified and isolated nucleic acid molecules (which may be in the form of DNA molecules), comprising at least a portion coding for Hin47 as typified by embodiments of the present invention. Such strains are generally available from clinical sources and from bacterial culture collections, such as the American Type Culture collection. Such strains include H. influenzae strains and other bacteria that produce a protein capable of generating antibodies that specifically recognize Hin47 fragment or analog thereof. Appropriate strains of Haemophilus may include:

H. influenzae type b strain MinnA;
H. influenzae type b strain Eagan;
H. influenzae non-typable strain SB33; or
H. influenzae non-typable strain PAK 12085.

Referring to FIG. 1, there is illustrated restriction maps of plasmids JB-1031-1-14 and JB-1068-2-2 that contain a portion encoding Hin47 protein from non-typable H. influenzae SB33. The nucleotide sequence of the Hin47 gene was determined and is shown in FIG. 2 along with the deduced amino acid sequence of the Hin47 protein. Referring to FIG. 3, there is shown an amino acid sequence alignment of H. influenzae Hin47 and the serine proteases htrA from Escherichia coli and htrA from Salmonella typhimurium. This alignment for the first time reveals the unexpected discovery of the present applicants that Hin47 is related to bacterial serine proteases and that Hin47 has protease activity. Hin47 has previously been reported to be an adhesin. The discovered protease activity thereof greatly limits the usefulness of natural Hin47 as an immunogen for vaccination and as an antigen in diagnostic uses. The sequence alignment shown in FIG. 3 revealed that the htrA proteins and Hin47 contain a GNSGGAL (SEQ ID NO: 17) sequence between residues 195 and 201 of the mature protein. The consensus sequence of the active site of serine proteases is GDSGGPK (SEQ ID NO: 18) (Brenner, 1988) and the active residue is serine. Thus, Serine-197 in Hin47 was mutated to produce an analog of Hin47 reduced in protease activity, in accordance with one embodiment of the invention. In a particular embodiment, Serine-197 was replaced by alanine. Amino acid residues 57 to 256 of Hin47 were further aligned with known proteases and the active site residues identified from the local homologies surrounding the residues of the catalytic triad (FIG. 4). There is a standard numbering system for serine proteases in which the catalytic triad residues are numbered as His-57, Asp-102 and Ser-195. These correspond to residues His-91, Asp-121 and Ser-197 in the sequential numbering system. Thus, referring to FIG. 4, there is shown a structure-based alignment of ten structurally determined serine proteases (SEQ ID NOS: 7 to 16) in which homologous residues are aligned primarily on the basis of similar locations in three-dimensional space. The location of many of the residues in the hydrophobic core of Hin47, as well as residues around the active site can be aligned reasonably well to identify functional amino acids of the Hin47 protease. Thus, other amino acid residues in Hin47 that contribute to protease activity of the protein include His-91 and Asp-121. In particular embodiments, His-91 may be replaced by alanine, lysine or arginine. In an additional embodiment, Asp-121 may be replaced by alanine or glutamic acid. Although the provision of an analog of Hin47 having reduced protease activity has been exemplified herein by particular amino acid substitution within Hin47 protein, the discovery of the protease activity and the methods of Hin47 expression, purification and analysis provided herein, allow for the production of other analogs having at least one other amino acid deleted or replaced or having at least one additional amino acid inserted into the Hin47 protein. In particular applications and embodiments, it may be desirable to simultaneously alter several amino acids of the Hin47 protein to particularly reduce the protease activity of Hin47. Accordingly, the present invention provides analogs of Hin47 protein having decreased protease activity due to single or multiple amino acid deletions, replacements or additions within the Hin47 protein.

Referring to FIG. 5, there is illustrated plasmids DS-1011-1-1 and DS-1048-2 which express a Hin47 analog serine-197→alanine in E. coli. FIG. 6 shows a flow diagram of a method for the purification of the Hin47 analog from E. coli inclusion bodies.

FIG. 7 shows the reduced protease activity of the Hin47 serine-197→alanine analog on the substrate β-casein and demonstrates the analog to have less than about 10% of the protease activity of natural Hin47 protein. Thus, in one embodiment of the invention, there is provided an analog of Hin47 having a protease activity of less than about 10% of the protease activity of natural Hin47 and such analog may specifically have amino acid Serine-197 replaced by alanine.

Referring to FIG. 8, there is illustrated an analysis of the increased stability of an analog of Hin47 as provided herein. Thus, in one embodiment of the present invention, there is provided an analog of Hin47 protein having increased thermal stability, and such analog may specifically have amino acid serine-197 replaced by alanine.

Referring to FIG. 9, there is illustrated the proteolytic degradation of a non-Hin47 Haemophilus antigen by Hin47 and a Hin47 analog as provided herein. Thus, in accordance with a further embodiment of the present invention, there is provided an analog of Hin47 compatible with a second non-Hin47 protein and such analog may specifically have amino acid Serine-197 replaced by alanine.

Referring to FIG. 10 and Table 1, there is illustrated the comparative immunogenicity of unmodified Hin47 and a Hin47 analog having reduced protease activity in mice. The Hin47 protein and Hin47 analog had comparable immunogenicity. Thus, in a particular embodiment, there is provided an analog of Hin47 having reduced protease activity and having substantially the same immunogenic properties of natural Hin47 protein. Such analog may specifically have amino acid Serine-197 replaced by alanine.

Referring to Table 2, there is shown the immunoprotective properties of an analog of Hin47 having reduced protease activity against Hib in the infant rat model of bacteraemia, according to an embodiment of the invention and such analog may specifically have amino acid Serine-197 replaced by alanine.

In accordance with another aspect of the present invention, there is provided a vaccine against Haemophilus or other bacterial pathogens that produce Hin47 or a protein capable of inducing antibodies that specifically recognize Hin47, comprising an immunogenically-effective amount of an immunoprotective analog of Hin47 as provided herein or a nucleic acid molecule having a sequence encoding a Hin47 analog as provided herein, and a physiologically-acceptable carrier therefor. The provided analogs also may be used as a carrier protein for hapten, polysaccharides or peptides to make a conjugate vaccine against antigenic determinants unrelated to Hin47.

As will be apparent from the following disclosure, the present invention further provides plasmids and novel strains of bacteria for production of Hin47 analogs as provided herein.

The purified and isolated DNA molecules comprising at least a portion coding for an analog of *Haemophilus influenzae* Hin47 protein having reduced protease activity compared to natural Hin47 typified by the embodiments described herein, are advantageous as nucleic acid probes for the specific identification of Haemophilus strains in vitro or in vivo. The Hin47 analogs encoded by the DNA molecules provided herein are useful as diagnostic reagents as antigens or for the generation of anti-Hin47 antibodies, antigens for the vaccination against the diseases caused by species of Haemophilus and other bacterial pathogens that produce a protein capable of producing antibodies that specifically recognise Hin47 and for detecting infection by Haemophilus and other such bacteria.

In additional embodiments of the present invention, the Hin47 analogs having reduced protease activity as provided herein may be used as carrier molecules to prepare chimeric molecules and conjugate vaccines (including glycoconjugates) against pathogenic bacteria, including encapsulated bacteria. Thus, for example, glycoconjugates of the present inventions may be applied to vaccinations to confer protection against disease and infection caused by any bacteria having polysaccharide antigens including lipooligosaccharides (LOS) and PRP. Bacterial pathogens may include, for example, *Haemophilus influenzae, Streptococcus pneumoniae, Escherichia coli, Neisseria meningitidis, Salmonella typhi, Streptococcus mutans, Cryptococcus neoformans*, Klebsiella, *Staphylococcus aureus* and *Pseudomonas aeruginosa*. Particular antigens which can be conjugated to analogs of Hin47 and methods to achieve such conjugations are described in applicants published PCT application WO 94/12641 which is hereby incorporated by reference thereto.

In another embodiment, the carrier function of Hin47 analogs may be used, for example, to induce immunity toward abnormal polysaccharides of tumor cells, or to produce anti-tumor antibodies that can be conjugated to chemotherapeutic or bioactive agents.

Accordingly, the present invention provides the primary sequence and the preparation of an analog of Hin47 of *H. influenzae* that can be used in the prevention and diagnosis of diseases caused by *H. influenzae*. In particular, the inventors discovered that the Hin47 analog can elicit protective immune responses against live *H. influenzae* type b bacterial challenge. Thus, the present inventions have utility in vaccines. The invention also discloses the nucleotide sequences of the gene encoding the Hin47 analog. These DNA segments may be used to provide an immunogen essentially free from other *H. influenzae* antigens, such as PRP and lipooligosaccharides (LOS), through, the application of recombinant DNA technology. The Hin47 analog protein, may be produced in a suitable expression system, such as *E. coli*, Haemophilus, Bacillus, Bordetella Fungi, Yeast, Baculovirus, Poxvirus, vaccinia or mammalian expression systems. The present disclosure further provides novel techniques which can be employed for preparing essentially pure Hin47 analogs.

It is clearly apparent to one skilled in the art, that the various embodiments of the present invention have many applications in the fields of vaccination, diagnosis, treatment of, for example, Haemophilus infections, and infections with other bacterial pathogens that produce proteins capable of producing antibodies that specifically recognize Hin47 and the generation of immunological reagents. A further non-limiting discussion of such uses is further presented below.

1. Vaccine Preparation and Use

Immunogenic compositions, suitable to be used as vaccines, may be prepared from Hin47 analogs as disclosed herein. The vaccine elicits an immune response in a subject which produces antibodies, including anti-Hin47 antibodies and antibodies that are opsonizing or bactericidal. Should the vaccinated subject be challenged by Haemophilus or other bacteria that produce proteins capable of producing antibodies that specifically recognize Hin47, the antibodies bind to and inactivate the bacterium. Furthermore, opsonizing or bactericidal anti-Hin47 antibodies may also provide protection by alternative mechanisms.

Immunogenic compositions including vaccines may be prepared as injectables, as liquid solutions or emulsions. The Hin47 analogs may be mixed with pharmaceutically acceptable excipients which are compatible with the Hin47 analog. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Methods of achieving adjuvant effect include the use of agents such as aluminum hydroxide or phosphate (alum), commonly used as 0.05 to 0.1 percent solution in phosphate buffered saline. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the Hin47 analogs. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the Hin47 analogs. Suitable regimes for initial administration and booster doses are also variable, but may include an initial administration followed by subsequent administrations. The dosage may also depend on the route of administration and will vary according to the size of the host.

The concentration of antigen in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

The nucleic acid molecules encoding the Hin47 analog of the present invention may also be used directly for immunization by administration of the DNA directly, for example, by injection for genetic immunization or by constructing a live vector, such as Salmonella, BCG, adenovirus, poxvirus, vaccinia or poliovirus. A discussion of some live vectors that have been used to carry heterologous antigens to the immune system are discussed in, for example, O'Hagan (1992). Processes for the direct injection of DNA into test subjects for genetic immunization are described in, for example, Ulmer et al, 1993.

2. Immunoassays

The Hin47 analogs of the present invention are useful as immunogens for the generation of anti-Hin47 antibodies, as antigens in immunoassays including enzyme-linked immunosorbent assays (ELISA), RIAs and other non-enzyme linked antibody binding assays or procedures known in the art for the detection of anti-bacterial, Haemophilus, and anti-Hin47 antibodies. In ELISA assays, the Hin47 analogs, are immobilized onto a selected surface, for example, a surface capable of binding proteins such as the wells of a polystyrene microtiter plate. After washing to remove incompletely adsorbed Hin47 analogs, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound Hin47 analogs, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

3. Use of sequences as Hybridization Probes

The nucleic acid molecules of the present invention, having the sequence of the hin47 analog gene, allow for the identification and cloning of the Hin47 genes from any species of Haemophilus and other bacteria that produce proteins capable of producing antibodies that specifically recognize Hin47.

The nucleic acid molecules having the sequence encoding the Hin47 analog of the present invention are useful for their ability to selectively form duplex molecules with complementary stretches of other hin47 genes. Depending on the application, a variety of hybridization conditions may be employed to achieve varying degrees of selectivity of the probe toward the other hin47 genes. For a high degree of selectivity, relatively stringent conditions are used to form the duplexes, such as low salt and/or high temperature conditions, such as provided by 0.02 M to 0.15 M NaCl at temperatures of between about 50° to 70° C. For some applications, less stringent hybridization conditions are required, such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results.

In a clinical diagnostic embodiment, the nucleic acid molecules encoding the hin47 genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, calorimetric indicator substrates are known which can be employed to provide a means visible to the human eye or spectrophotometrically, to identify specific hybridization with samples containing hin47 gene sequences.

The nucleic acid molecules comprising hin47 genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the hin47 genes of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label.

4. Expression of the Genes encoding analogs of Hin47 having reduced protease activity Vectors perhaps containing replicon and control sequences which are derived from species compatible with the host cell may be used for the expression of the Hin47 analog genes as provided herein in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda "GEM"-11 may be utilized in making recombinant phage vectors which can be used to transform host cells, such as E. coli LE392.

Promoters commonly used in recombinant DNA construction include the β-lactamase (penicillinase) and lactose promoter systems (Chang et al, 1979; Goeddel et al, 1980) and other microbial promoters, such as the T7 promoter system (U.S. Pat. No. 4,952,496). Details concerning the nucleotide sequences of promoters are known, enabling a skilled worker to ligate them functionally with plasmid vectors. The particular promoter used will generally be a matter of choice depending upon the desired results. Hosts that are appropriate for expression of the Hin47 analogs include E. coli, Bacillus species, Haemophilus Bordetella fungi, yeast, mammalian cells or the baculovirus expression system may be used.

Thus, in accordance with the invention, it may be preferred to make the Hin47 analog protein by recombinant methods. Particularly desirable hosts for expression in this regard include Gram positive bacteria which do not have LPS and are therefore endotoxin free. Such hosts include species of Bacillus and may be particularly useful for the production of non-pyrogenic Hin47 analog.

Biological Deposits

Plasmid DS-1011-1-1 (pT7/Hin47*) that contains a portion coding for a Hin47 analog that is described and referred to herein has been deposited with the American Type Culture Collection (ATCC) located at Rockville, Md., USA, pursuant to the Budapest Treaty and prior to the filing of this continuation-in-part application on Jul. 27, 1994 under Accession No. 75845. Samples of the deposited plasmid will become available to the public upon grant of a patent based upon this United States patent application. The invention described and claimed herein is not to be limited in scope by plasmid deposited, since the deposited embodiment is intended only as an illustration of the invention. Any equivalent or similar plasmids that encode similar or equivalent antigens as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example illustrates the cloning of the hin47 gene from non-typable H. influenzae strain SB33.

Chromosomal DNA was prepared from H. influenzae strain SB33, and an EMBL3 library was prepared and screened with a labelled oligonucleotide probe specific for the 5'-end of hin47. Non-typable H. influenzae strain SB33 was grown on Mueller-Hinton agar or in brain heart infusion broth as described by Harkness et al, 1992. Chromosomal DNA was prepared as follows: cells from 50 ml of culture were pelleted by centrifugation at 5000 rpm for 15 to 20 min, at 4° C., in a Sorvall RC-3B centrifuge. The cell pellet was resuspended in 10 ml of TE (10 mM Tris/HCl, 1 mM EDTA, pH 7.5), pronase was added to 500 $\mu$g ml$^{-1}$ and SDS to 1%. The sample was incubated at 37° C. until a clear lysate was obtained. The lysate was gently extracted once with Tris-saturated phenol (pH 7.4), once with Tris-saturated phenol/chloroform (1:1) and once with chloroform. The final aqueous phase was dialysed at 4° C for 24 h against 1M NaCl, followed by 24 h against TE.

An EMBL3 library was prepared by partial digestion of SB33 chromosomal DNA with Sau3A I, followed by size fractionation either on a 10 to 30% sucrose gradient in TNE (20 mM Tris/HCl, 5 mM NaCl, 1 mM EDTA, pH 8.0) or by preparative gel electrophoresis. Fractions containing DNA fragments greater than 5 kb in length were pooled, precipitated and ligated with BamH I arms of EMBL3 (Promega). The ligation mixture was packaged using a Gigapack II packaging kit and plated onto E. coli LE392 cells. The libraries were amplified and stored at 4° C. in the presence of 0.3% chloroform.

Plaques were lifted onto nitrocellulose filters for hybridization with a $^{32}$P-labelled oligonucleotide probe (3026.SL). The oligonucleotide sequence was ATGAAAAAAA-CACGTTTTGTATTAAATAGTATTGCACTTGG (SEQ ID NO: 3) corresponding to the N-terminal amino acid sequence MKKTRFVLNSIALG (SEQ ID NO: 19). Phage DNA was prepared from putative plaques and the insert DNA was excised by Sal I digestion and cloned into pUC8-BgXb digested with Sal I. Plasmids JB-1031-1-14 and JB-1068-2-2 (FIG. 1) were selected for further analysis.

Example 2

This Example illustrates the characterization and sequence analysis of the hin47 gene and deduced amino acid sequence of the Hin47 protein from NTHi strain SB33.

Restriction mapping and Southern blot analysis of clones JB-1031-1-14 and JB-1068-2-2 localized the hin47 gene on a 4.7 kb BamH I/BamH I or a 2.7 kb BamH I/Pst I DNA fragment. The 4.7 kb BamH I/BamH I fragment from JB-1068-2-2 was subcloned into pUC8/BgXb generating plasmid DS-755-1. The 3.1 kb BamH I to Xba I fragment of DS-755-1 was subcloned into pUC18 generating plasmid JB-1165-1 which has restriction sites suitable for the Erase-a-base (Promega) procedure (FIG. 1). This technique generates successive clones with increasing truncations of insert DNA, with the deletions occurring from the same end. The resultant nested set of clones can be sequenced rapidly using a universal primer.

DNA from plasmid JB-1165-1 was digested with BamH I and Sac I and subjected to exoIII digestion using an Erase-a-base kit. The resultant set of truncated plasmids was analysed by agarose gel electrophoresis and representative plasmids were selected for sequence analysis.

Plasmid DNA for sequencing was prepared by a modification of the procedure of Holmes and Quigley, 1981. Briefly, the cell pellet from 50 ml of culture was resuspended in 10 ml STET (8% sucrose, 5% Triton X-100, 50 mM EDTA, and 50 mM Tris/HCl, pH 8.0), lysozyme (2.5 mg) was added and the mixture was boiled for 2 min. The sample was spun at 14,000 rpm in a Sorvall RC 5B for 20 minutes and the supernatant was precipitated with an equal volume of isopropanol, washed with 70% ethanol then absolute ethanol, and then air dried. The pellet was resuspended in 0.9 ml of TE, then 20 µl of 5 mg ml$^{-1}$ RNAse A were added, and the mixture was incubated at 37° C. for 15 min. After the addition of 500 µl of 1.5M NaCl/30% PEG, the mixture was incubated on ice for 30 min and the DNA was pelleted by centrifugation in an Eppendorf microfuge for 10 min. The pellet was resuspended in 400 µl of TE and extracted twice with Tris-saturated phenol (pH 7.4), twice with Tris-saturated phenol/chloroform (1:1) and twice with chloroform. The DNA was precipitated by adding 40 µl of 3M ammonium acetate and 1 ml of ethanol, washed with 70% ethanol and resuspended in distilled water.

DNA samples were sequenced using the ABI model 370A DNA sequencer and the dye terminator chemistry. The universal reverse primer was used with the nested set of clones to determine the sequence of the hin47 coding strand. Oligonucleotide primers of approximately 25 bases in length were used to confirm the sequence of the non-coding strand. The nucleotide sequence of the SB33 hin47 gene and the deduced amino acid sequence of the Hin47 protein are shown in FIG. 2. The nucleotide and N-terminal amino acid sequences of Hin47 presented at the ASM meeting, New Orleans, May 26 to 30, 1992 are indicated in lower case on FIG. 2. The amino terminal sequences of the SB33 Hin47 and this presented sequence are identical, establishing the identity of the cloned gene as hin47.

Example 3

This Example describes the discovery of serine protease activity of Hin47 protein.

The deduced amino acid sequence of Hin47 protein determined in Example 2 above was compared with all other known proteins in the Genbank data base. As described above, Hin47 protein is described in published PCT applications WO 94/00149, WO 92/11367 and WO 92/10936 to be an adhesin molecule of Haemophilus. It was, therefore, a surprising and unexpected discovery of the present invention that Hin47 protein has significant amino acid homology (55%) with the serine proteases E. coli htrA and S. typhimurium htrA and other proteases. These amino acid sequence homologies are shown in FIGS. 3 and 4. Furthermore, Hin47 protein was found to autodigest unless it was stored in the presence of a serine protease inhibitor, such as Pefablock.

Example 4

This Example illustrates the generation of the mutant hin47 gene by site-directed mutagenesis.

As explained above, H. influenzae Hin 47, E. coli htrA, and S. typhimurium htrA are all serine proteases. The consensus sequence of the active site of serine proteases is GDSGGPK (SEQ ID NO: 18) [Brenner, 1988] with serine being the active residue. The htrA proteins both have a GNSGGAL (SEQ ID NO: 17) sequence and in H. influenzae Hin47, there is the identical sequence between residues 195 and 201 of the mature protein. Thus, the serine residue at position 197 was selected for site-directed mutagenesis, to produce an analog of Hin47 with reduced protease activity.

An oligonucleotide CGCTCCACCAGCATTACCGCGG (SEQ ID NO: 20) was synthesized which would change the serine residue at 197 to an alanine. The hin47 gene was cloned into M13mp18 generating clone DS-981-3 and mutagenesis was performed using the Amersham In Vitro Site-Directed Mutagenesis kit. Clone DS-991-8 was confirmed by sequence analysis to contain the mutation Serine-197 to Alanine. This mutant hin47 gene is designated hin47*.

In addition a comparison of the amino acid sequence of Hin47 with other proteases (as shown in FIG. 4) revealed that amino acids His-91 and Asp-121 are sites appropriate for mutagenesis to produce an analog of Hin47 with reduced protease activity. By mutagenesis methods analogous to those described above, His-91 and/or Asp-121 are deleted or replaced by different amino acids. Such amino acid replacements may include His-91 to Alanine and Asp-121 to Alanine. Olignonucleotides to effect such mutagenesis include:

His-91→Ala-91 5' ATCAATAACAGCATTATTGGT 3' (SEQ ID NO: 21)
Asp-121→Ala-121 5' TAATGCAATTGCTGATAGTTC3' (SEQ ID NO: 22)

Many serine proteases are secreted in an inactive ('zymogen') form, and require clipping to expose their active sites. N terminal sequence analysis of mature natural Hin47 protein suggested the cleavage of the preprotein to occur at KFFFG DRFAEQ (SEQ ID NO: 23). Modifications of amino acids that prevent cleavage of the molecule to produce the active protease molecule can produce an analog of Hin47 having reduced protease activity.

Example 5

This Example illustrates the construction of plasmids expressing Hin47 Ser-197→alanine analog from E. coli.

The mutated hin47* gene from plasmid DS-991-8 was cloned into the pT7-7 expression vector to generate plasmid DS-1011-1-1 (FIG. 5). E.coli strain BL21/DE3 was transformed to generate E. coli strain DS-1018-3-1 which expresses Hin47 Ser-197→alanine analog upon induction.

In order to utilize tetracycline selection, the hin47* gene was cloned into pBR328. The Bgl II/Cla I T7/hin47* gene fragment from DS-1011-l-1 was cloned into pEVvrfl (Young and Davis, 1985) in order to generate a Bgl II/BamH I fragment which could be cloned into pUC-4K (Pharmacia) digested with BamH I. The resultant clone DS-1034-3 was digested with EcoR I and the T7/hin47* gene fragment cloned into pBR328 (Boehringer Mannheim Corporation) to generate plasmids DS-1048-2 and DS-1067-2. Electroporation of plasmid DNA into E. coli strain BL21/DE3 resulted in strains DS-1071-1-1 and DS-1071-3-1 which express the Hin47 Ser-197→alanine analog.

Example 6

This Example illustrates the expression of Hin47 Ser-197→alanine analog from *E. coli*.

An overnight culture of strains DS-1018-3-1, DS-1071-1-1, or DS-1071-3-1 were grown overnight in NZCYM media+3% dextrose+antibiotics (ampicillin at 25 μg ml$^{-1}$ or tetracycline at 10 μg ml$^{1}$), at 37° C., with shaking. A 1:40 dilution of the overnight culture was inoculated into the same medium and grown at 37° C. with shaking until the absorbance was $A_{578}$ approximately 0.3. A ⅟₁₀ volume of 10% lactose was then added to induce expression from the T7 promoter. Cell samples were harvested about 4 hours after induction by centrifuging culture samples at 5000 rpm for 10 min in a Sorvall RC-3B, at 4° C.

Example 7

This Example illustrates the extraction and purification of Hin47.

Hin47 was expressed as soluble protein in *E. coli*. The cell pellet from a 250 ml culture, prepared as described in Example 6, was resuspended in 40 ml of 50 mM Tris-HCl, pH 8.0, and disrupted by sonication (3×10 min, 70% duty circle). The extract was centrifuged at 20,000×g and the resulting supernatant which contained >95% of the soluble Hin47 protein was retained. This fraction was called "Hin47-extract".

This Hin47-extract was further purified on a DEAE Sephacel column. Forty ml of the Hin47-extract was applied onto a 20-ml DEAE Sephacel column equilibrated in 50 mM Tris-HCl, pH 8.0. Hin47 bound to the column under these conditions. The column was washed with 100 ml of 50 mM Tris-HCl, pH 8.0, and then washed with 100 ml of 50 mM Tris-HCl, pH 8.0 containing 20 mM NaCl. Hin47 was then eluted with 50 mM Tris-HCl, pH 8.0, containing 40 mM NaCl. The amount of Hin47 in the fractions was determined by the BCA protein assay. The purity of Hin47 was assessed by SDS-PAGE analysis. The fractions containing Hin47 were combined and stored at −20° C.

Example 8

This Example illustrates the extraction and purification of Hin47 Ser-197→alanine analog.

Hin47 Ser-197→alanine analog was expressed in inclusion bodies in *E. coli*. The cell pellet from a 250 ml culture, prepared as described in Example 6, was resuspended in 40 ml of 50 mM Tris-HCl, pH 8.0, and disrupted by sonication (3×10 min, 70% duty circle). The extract was centrifuged at 20,000×g and the resulting pellet was saved. The pellet was re-extracted with 40 ml of 50 mM Tris-HCl, 0.5% Triton X-100, 10 mM EDTA, pH 8.0. The suspension was sonicated 10 min at 70% duty circle. The extract was centrifuged at 300×g for 5 min. The resultant supernatant was centrifuged again at 20,000×g for 30 min and the resultant pellet was saved. The pellet was resuspended in 50 mM Tris-HCl, 0.5% Triton X-100, 10 mM EDTA, pH 8.0. The suspension was then mixed with 50 mM Tris-HCl, pH 8.0 containing 8 M urea. The final urea concentration in the mixture was adjusted to 2 M with 50 mM Tris-HCl, pH 8.0. Hin47 Ser-197→alanine analog was completely solubilized under these conditions. The final volume of the solution was 20 ml. This fraction is called "Hin47 analog-extract". The Hin47 analog-extract was further purified on a DEAE Sephacel column. Twenty ml of Hin47 analog-extract was applied onto a 10 ml DEAE Sephacel column equilibrated in 50 mM Tris-HCl, pH 8.0. Hin47 Ser-197→alanine analog bound to the column under these conditions. The column was washed with 50 mM Tris-HCl, pH 8.0, and Hin47 analog was eluted with 50 mM Tris-HCl, pH 8.0, containing 30 mM NaCl. The amount of Hin47 analog in the fractions was determined by the BCA protein assay. The purity of Hin47 analog was assessed by SDS-PAGE analysis (FIG. 6). The fractions containing Hin47 analog were combined and stored at −20° C.

Example 9

This Example illustrates the protease activity of Hin47 and Hin47 Ser-197→alanine analog.

The enzymatic activity of Hin47 and Hin47 Ser-197→alanine analog was analyzed using β-casein as a substrate (FIG. 7). The reaction mixtures contained 5 μg of β-casein and either Hin47 or Hin47 analog. The reaction was carried out at 37° C. for two hours, and then stopped by adding the SDS-sample buffer and instantly heating the sample at 100° C. for 5 min. The aliquots were analyzed by SDS-PAGE. As shown in FIG. 7, digestion of β-casein by Hin47 was more obvious after two hours (panel A, lane 1) in comparison to the fractions containing Hin47 analog (panel A, lane 2) or without any exogenous proteins (panel A, lane 3). The presence of Hin47 or Hin47 analog in these mixtures were confirmed by immuno-blotting using a monoclonal antibody to Hin47 (FIG. 7, panel C, lanes 1 and 2).

The protease activities of Hin47 and Hin47 Ser-197→alanine analog were also compared by analyzing the autodigestion of Hin47 or Hin47 analog at 4° C. and −20° C. The purified Hin47 or analog were stored at either 4° C. or −20° C. for up to 20 days. Aliquots were taken on days 0, 10 and 20 and the stability of Hin47 or analog was analyzed by immuno-blotting using a Hin47 monoclonal antibody (FIG. 8). The analog was much more stable than Hin47 up to 20 days when stored at either 4° C. or −20° C.

To further examine the protease activity of the Hin47 Ser-197→alanine analog, the ability of Hin47 or analog to degrade an 80-kDa *H. influenzae* recombinant antigen was examined. Thus, a mixed antigen study was performed to determine the proteolytic effect of Hin47 or Hin47 analog on another antigen. An 80 kDa *H. influenzae* recombinant protein (TBP1) was chosen for this study in order to distinguish it from the Hin47 or analog protein (47 kDa). Five mixtures were formulated as follows: 80-kDa protein alone; 80-kDa protein+Hin47; 80-kDa protein+analog; Hin47 alone; and analog alone. The amount of each protein in the mixture was 5 μg. The mixtures were stored at 4° C. up to four weeks. Aliquots were taken on days 0, 7, 14 and 28 for analysis by SDS-PAGE (FIG. 9). Both the 80 kDa protein and Hin47 were largely degraded after one week (lanes 2 and 4). In contrast, the 80 kDa protein in combination with Hin47 analog remained intact after one week, and showed only slight degradation even after four weeks (lane 3).

Example 10

This Example illustrates the comparative immunogenicity of Hin47 and Hin47 analog in mice. The results of a study to determine the comparative immunogenicity of Hin47 and the Hin47 Ser-197→alanine analog are shown in FIG. 10. Thus, groups of five Balb/c mice were injected three times (as indicated by arrows) s.c. on days 1, 29 and 43 with 1μg dose of either Hin47 or Hin47 analog in the presence of $AlPO_4$ (1.5 mg per dose). Blood samples were taken on days 14, 28, 42 and 56 (as indicated by bleeds 1, 2, 3 and 4, respectively) for analyzing the anti-Hin47 antibody titers by EIAs. The determination of anti-Hin47 antibodies in mouse sera was performed as described by Panezutti et al. (1993). Microtiter wells were coated with 1 μg of either Hin47 or analog for 16 hours at room temperature. The plates were then blocked with 0.1% (w/v) bovine serum albumin in PBS. The mouse sera were serially diluted, added to the wells, then incubated for one hour at room temperature. Affinity-purified F(ab')$_2$ fragments of goat anti-mouse IgG (Fc specific) antibody conjugated to horseradish peroxidase were used as the second antibody. The reactions were developed using tetramethylbenzidine (TMB/H$_2$O$_2$) and absorbencies were measured at 450 nm (using 540 nm as a reference wavelength) in a Flow Multiskan MCC microplate reader. The reactive titer of an antiserum was defined as the reciprocal of the dilution consistently showing a two-fold increase in absorbance over that obtained with the pre-bleed serum sample. As can be seen from FIG. 10, both Hin47 and the Hin47 analog elicited comparable IgG titers in mice regardless of whether Hin47 or mutant was used as an antigen in EIAs.

To further examine the immune response to Hin47 or the Hin47 Ser-197→alanine analog, the subclasses of anti-Hin47 IgG in mouse sera were determined. Microtiter wells were coated with 1 μg of purified Hin47 or analog. The final bleed of mouse serum samples from the comparative immunogenicity study (as described above) were pooled and tested in EIAs. Rat anti-mouse IgG$_1$, IgG$_{2a}$, IgG$_{2b}$ antibodies conjugated horseradish peroxidase and rabbit anti-mouse IgG$_3$ conjugated to horseradish peroxidase were used as reagents in EIAs. The working dilution of each conjugate was determined using purified antibody subclasses to avoid cross reactivity. The reactive titers were determined as described above. As shown in Table 1 below, the IgG-subclass profile induced in mice by either Hin47 or Hin47 analog were identical, regardless of whether Hin47 or analog was used as a solid antigen in the EIAs. The predominant IgG response in both groups of mouse sera was of the IgG$_1$ isotype. Hence, the Hin47 analog exhibited substantially the same immunogenic properties as the natural protein.

Example 11

This Example illustrates the immunoprotective properties of Hin47 and Hin47 Ser-197→alanine analog.

The immunoprotective properties of Hin47 and the Hin47 Ser-197→alanine analog were analyzed by the ability of Hin47 specific antisera to protect infant rats against *H. influenzae* type b strain MinnA in a bacteremia model. The results of this study are shown in Table 2 below. Groups of nine 6-day old Wistar infant rats were inoculated subcutaneously (s.c.) on the dorsum close to the neck with 0.1 mL of either a rabbit anti-Hin47 analog antiserum or the corresponding prebleed serum. Twenty-four hours later, the animals were challenged intraperitoneally (i.p.) with 700 cfu of freshly grown Hib strain MinnA. Blood samples were collected 20 hours post-challenge and plated onto chocolate agar plates. Bacterial colonies were counted after 24 hours. As shown in Table 2, three out of nine animals in the group inoculated with anti-Hin47 analog antiserum did not show any bacteremia in their blood. Only one mouse in the group inoculated with anti-Hin47 analog antiserum (11%) had a higher bacteria recovery from the blood sample compared to mice inoculated with prebleed serum. In contrast, bacteria were recovered from all the nine mice inoculated with pre-bleed serum. Four out of nine animals (44%) in the group inoculated with pre-bleed serum showed high levels (500. to 1,000) of bacteria recovered in blood samples.

SUMMARY OF DISCLOSURE

In summary of this disclosure, the present invention provides a novel analog of *Haemophilus influenzae* Hin47 protein which has a decreased protease activity of less than about 10% of that of the natural Hin47 protein as well as isolated and purified DNA molecules encoding the same.

TABLE 1

Hin47 IgG titers in mouse immune sera

| | IgG titers in Group #1* | | IgG titers in Group #2* | |
|---|---|---|---|---|
| IgG Suclass | To Hin47 | To Mutant | To Hin47 | To Mutant |
| IgG(H + L) | 102,400 | 102,400 | 102,400 | 102,400 |
| IgG$_1$ | 25,600 | 25,600 | 25,600 | 25,600 |
| IgG$_{2a}$ | <100 | <100 | <100 | <100 |
| IgG$_{2b}$ | 400 | 400 | 400 | 400 |
| IgG$_3$ | <100 | <100 | <100 | <100 |

Group #1: Immune sera were pooled from a group of five mice received Hin47 immunization.

Group #2: Immune sera were pooled from a group of five mice received Hin47 mutant immunization.

Plates were coated with either Hin47 or mutant protein.

TABLE 2

Protective ability of rabbit Anti-Hin47 Mutant antiserum against Hib in infant rat model of bacteremia

| | Number of Animals cfu of Bacteria/2.5 μL Blood | | | | |
|---|---|---|---|---|---|
| Antibody | Av.0 | Av.50 (10–100) | Av.200 (100–300) | Av.650 (300–1,000) | Total Animals |
| Anti-Hin47* | 3 | 3 | 2 | 1 | 9 |
| Prebleed | 0 | 4 | 1 | 4 | 9 |

Groups of nine 6-day old infant rats were immunized s.c. with either a rabbit anti-Hin47 mutant antiserum or the corresponding prebleed serum. Animals were challenged i.p. with 700 cfu *H. influenzae* strain MinnA after 24 hours. The blood samples were taken at 20 hours after the challenge.

Anti-Hin47* antibody: rabbit immune serum raised against purified Hin47 mutant in CFA/IFA.

Average bacteria recovery from immunized group: 100 cfu per 2.5 μL of blood; from control group: 290 cfu per 2.5 μL of blood.

REFERENCE LIST

1. Zangwill et al, 1993 MMWR 42:1–15.
2. Schoendorf et al, 1994 Pediatrics 93:663–8.
3. Brenner et al, 1988 Nature 334:528–530.
4. O'Hagan 1992 Clin. Pharmokinet. 22:1–10.
5. Ulmer et al, 1993 Curr. Opinion. Invest. Drugs 2:983–989.
6. Chang et al, 1978 Nature 275:617.
7. Goeddel et al 1980 Nucl. Acid. Res. 8:4057.
8. Harkness et al, 1992 J. Bacteriol. 174:2425–2430.
9. Loeb et al, 1987 Infec. Immun. 55:2612–2618.
10. Holmes and Quigley 1981. Analyt. Biochem. 114:193–197.
11. Young and Davis 1985 Gene 38:31–38.
12. Panezutti et al, 1993 Infec. Immun. 61:1867–72.

What we claim is:

1. A method of generating an immune response in a host, comprising administering thereto an immunoeffective amount of an immunogenic composition comprising an immunoeffective amount of an isolated and purified nucleic acid molecule comprising a mutant *Haemophilus influenzae* hin47 gene encoding an analog of *Haemophilus influenzae* Hin47 protein having a decreased protease activity which is less than about 10% of that of natural Hin47 protein and having substantially the immunogenic properties of the Hin47 protein.

2. The method of claim 1 wherein at least one codon of a wild-type hin47 gene encoding an amino acid contributing to protease activity which is the codon encoding an amino acid selected from the group consisting of amino acids 91, 121 and 195 to 201, has been deleted or replaced by a codon encoding a different amino acid to provide the reduced protease activity.

3. The method of claim 2 wherein the at least one codon is that encoding Serine-197.

4. The method of claim 2 wherein the codon encoding His-91 is replaced by a codon encoding His-91 is replaced by a codon encoding alanine, lysine or arginine.

5. The method of claim 2 wherein the codon encoding Asp-121 is replaced by a codon encoding alanine or glutamic acid.

6. The method of claim 2 wherein said mutant gene is formed by site-directed mutagenesis of a wild-type hin47 gene.

7. The method of claim 3 wherein the codon encoding Serine-197 is replaced by a codon encoding alanine.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
       (A) LENGTH: 2894 base pairs
       (B) TYPE: nucleic acid
       (C) STRANDEDNESS: single
       (D) TOPOLOGY: linear (xi) SEQUENCE DESCRIPTION: SEQ ID NO:1:

```
GGATCCGTTA ATACTGAAAT AAATGGCACA CCTTTTTCAC GCATTTGGGC AAGTACAGCA       60

CTGGTTTTTG CCATTTGCAT TAAAGAGAAT AATGCTTCCT GCATACGAGC ACCACCACTC      120

GCAGAGAAAC ATACAAACGG ACAATTCATT TCCATCGCTT TTTCAGCCGC TTTAACAAAT      180

TTTGCACCAA CTACAGAACC CATTGAACCG CCCATAAAAG CAAAGTTCGA TGCAGCCACA      240

ACAATTGGCA TATCATAAAG TGTACCTGTC ATAGTAATTA GCGCATCTTT CTCGCCCGTT      300

TCTTTTTGTG CCGCATTGAT ACGATCTTTA TATTTCTTTA AATCTTTAAA TTTTAAAATA      360

TCTTTTGGTT CTAAATCTGC CGCAATTTCT TGGCTTGAAT CTTCGTCCAA TAAATTTAAT      420

AAACGCTCAC GAGCATCAAT ACGCATATGA TGACCACATT TCGGGCAAAC ATACAGATTA      480

CGTTTGAGTT CTTCACTATA AAGTACTTGT TCACAAGCAG TACATTTTGT CCATACGCCT      540

TCTGGCACAT TGGCTTTTCG AGTGGAAGAA GAAGGACTTT TACTAAAAAT TCGGTTAATC      600

CAGCTCATTT TTTGACCTTT TTATTGACTA GAAAATTGCG CGTATTAGAA CATAAATTTA      660

TAGAATTTGC TACTTGTAAG ACCGTTTTTG TACTGCTCCG ATTTCCTTTT AAACAAGATA      720

ATTTGCTCTC CTCTTATTGA ACATTTTTTT TATTTTTTTG TCTTACTGAC CACGTTATCT      780

GAAATTTATT TTGGAGTATT TATGAAAAAA ACACGTTTTG TACTAAATAG TATTGCACTT      840

GGATTAAGTG TATTAAGCAC ATCATTTGTT GCTCAAGCCA CTTTGCCAAG TTTTGTTTCG      900

GAACAAAACA GTCTTGCACC AATGTTAGAA AAAGTACAAC CTGCCGTTGT CACTCTTTCC      960

GTTGAAGGAA AAGCTAAAGT AGATTCTCGT TCTCCTTTCC TAGACGATAT TCCTGAAGAA     1020

TTTAAATTCT TCTTTGGCGA TCGTTTTGCC GAACAATTTG GTGGACGTGG AGAATCAAAG     1080

CGTAACTTCC GTGGTTTAGG TTCTGGTGTC ATTATTAATG CAAGCAAAGG CTATGTTTTA     1140

ACCAATAATC ATGTTATTGA TGAAGCTGAT AAAATTACCG TGCAATTACA AGATGGGCGT     1200

GAATTTAAAG CAAAATTAGT GGGTAAAGAT GAACTATCAG ATATTGCATT AGTACAGCTT     1260

GAAAAACCAA GTAATTTAAC AGAAATCAAA TTTGCTGATT CCGACAAATT ACGCGTAGGC     1320

GATTTCACTG TTGCAATCGG TAATCCATTT GGTTTAGGTC AAACTGTGAC ATCAGGTATT     1380

GTTTCTGCAT TGGGTCGTTC AACAGGTTCT GACAGTGGCA CTTATGAAAA CTATATTCAA     1440

ACCGATGCAG CAGTAAACCG CGGTAATTCG GGTGGAGCGT TAGTAAACTT AAATGGCGAA     1500

CTTATTGGAA TTAATACCGC AATTATTTCT CCAAGCGGTG GCAATGCAGG AATTGCCTTT     1560

GCGATTCCAA GTAATCAAGC AAGCAATTTA GTGCAACAAA TTTTAGAATT TGGTCAAGTG     1620

CGTCGCGGAT TGCTTGGTAT TAAAGGTGGC GAACTCAATG CTGATTTAGC CAAAGCCTTT     1680

AATGTAAGCG CGCAACAAGG CGCATTTGTA AGTGAAGTTT TACCGAAATC TGCTGCTGAA     1740

AAAGCAGGAC TTAAAGCGGG CGATATTATC ACGGCGATGA ACGGTCAAAA AATCTCAAGT     1800

TTCGCTGAAA TTCGTGCAAA AATCGCAACC ACTGGTGCAG GCAAAGAGAT TAGCTTGACT     1860
```

-continued

```
TACTTACGTG ATGGCAAATC CCACGACGTT AAAATGAAAT TACAAGCGGA TGATAGTAGC       1920

CAACTTTCCT CAAAAACTGA GTTGCCTGCA TTAGATGGTG CAACATTGAA AGACTACGAT       1980

GCTAAAGGCG TTAAAGGAAT TGAAATCACA AAAATTCAAC CTAATTCGCT GGCTGCACAA       2040

CGTGGTTTAA AATCGGGCGA TATTATTATT GGTATTAATC GTCAAATGAT CGAAAACATT       2100

CGTGAATTAA ATAAAGTGCT TGAAACTGAA CCGTCAGCAG TTGCACTTAA TATTTTACGA       2160

GGTGACAGTA ATTTCTATTT ATTAGTGCAA TAATCTGCTT GATATATTTA AGAAAAAGT       2220

CCGATCACAA TGATCGGGCT TCTTTTTATG CAGCAATCGT TCTTAACAAA TCCACCACAA       2280

ATTCTAACCG CACTTTGTTA TCAGATAAAT CTTTCATGAA CTTAAATTTT AATGGGCCAT       2340

CAAATCGATA CACAATAGGT TCTTTTTGAA TTAATTGAAT AAATTTATCT GGATTCACTT       2400

GTGCTTTTGC TGAAAACTCA ATAAAACCGC CTTGTGTTCC TGCATCAATT CGCACAACTT       2460

TCAACGGCTC AACCAACAAA CGCAATTCTG CAATTTGCAG TAAATTTTTT GTTGCATCAG       2520

GCAATAATCC GAATCGATCT ATTAACTCAA CTTTTAATTC ATCTAATTCT GCTTTACTCT       2580

CTGCTGCAGC AATGCGTTTA TAAAAGGATA AACGCATATT CACGTCTCCT AGATAATCAT       2640

CAGGCAGTAA AGCAGGCACA CGCAATTCAA TATCCGCTTG TTGTTGCGTC AATTCTTCTA       2700

ATGATGGTTC ACGCCCTTCT TTTAACGCTT TAACCGCTGC ATCCAATAAT TCCATATAAA       2760

GCGAAAAACC GATGCTTTCA ATTTGTCCAC TTTGTTCGTT TCCAAGTAAT TCGCCGGCAC       2820

CACGAATCTC TAAATCGTGG GTTGCCAAGA TAAAACCAGC CCCAAGATTA TCAAGATTTT       2880

CCAAGGCATC TAGA                                                       2894
```

(2) INFORMATION FOR SEQ ID NO:2:

(i) SEQUENCE CHARACTERISTICS:
        (A) LENGTH: 463 amino acids
        (B) TYPE: amino acid
        (C) STRANDEDNESS: single
        (D) TOPOLOGY: linear (xi) SEQUENCE DESCRIPTION: SEQ ID NO:2:

```
Met Lys Lys Thr Arg Phe Val Leu Asn Ser Ile Ala Leu Gly Leu Ser
 1               5                  10                  15

Val Leu Ser Thr Ser Phe Val Ala Gln Ala Thr Leu Pro Ser Phe Val
            20                  25                  30

Ser Glu Gln Asn Ser Leu Ala Pro Met Leu Glu Lys Val Gln Pro Ala
        35                  40                  45

Val Val Thr Leu Ser Val Glu Gly Lys Ala Lys Val Asp Ser Arg Ser
    50                  55                  60

Pro Phe Leu Asp Asp Ile Pro Glu Glu Phe Lys Phe Phe Gly Asp
65                  70                  75                  80

Arg Phe Ala Glu Gln Phe Gly Gly Arg Gly Glu Ser Lys Arg Asn Phe
                85                  90                  95

Arg Gly Leu Gly Ser Gly Val Ile Ile Asn Ala Ser Lys Gly Tyr Val
            100                 105                 110

Leu Thr Asn Asn His Val Ile Asp Glu Ala Asp Lys Ile Thr Val Gln
        115                 120                 125

Leu Gln Asp Gly Arg Glu Phe Lys Ala Lys Leu Val Gly Lys Asp Glu
    130                 135                 140

Leu Ser Asp Ile Ala Leu Val Gln Leu Glu Lys Pro Ser Asn Leu Thr
145                 150                 155                 160

Glu Ile Lys Phe Ala Asp Ser Asp Lys Leu Arg Val Gly Asp Phe Thr
                165                 170                 175
```

```
Val Ala Ile Gly Asn Pro Phe Gly Leu Gly Gln Thr Val Thr Ser Gly
            180                 185                 190

Ile Val Ser Ala Leu Gly Arg Ser Thr Gly Ser Asp Ser Gly Thr Tyr
            195                 200                 205

Glu Asn Tyr Ile Gln Thr Asp Ala Ala Val Asn Arg Gly Asn Ser Gly
            210                 215                 220

Gly Ala Leu Val Asn Leu Asn Gly Glu Leu Ile Gly Ile Asn Thr Ala
225                 230                 235                 240

Ile Ile Ser Pro Ser Gly Asn Ala Gly Ile Ala Phe Ala Ile Pro
                245                 250                 255

Ser Asn Gln Ala Ser Asn Leu Val Gln Gln Ile Leu Glu Phe Gly Gln
            260                 265                 270

Val Arg Arg Gly Leu Leu Gly Ile Lys Gly Gly Glu Leu Asn Ala Asp
            275                 280                 285

Leu Ala Lys Ala Phe Asn Val Ser Ala Gln Gln Gly Ala Phe Val Ser
            290                 295                 300

Glu Val Leu Pro Lys Ser Ala Ala Glu Lys Ala Gly Leu Lys Ala Gly
305                 310                 315                 320

Asp Ile Ile Thr Ala Met Asn Gly Gln Lys Ile Ser Ser Phe Ala Glu
                325                 330                 335

Ile Arg Ala Lys Ile Ala Thr Thr Gly Ala Gly Lys Glu Ile Ser Leu
            340                 345                 350

Thr Tyr Leu Arg Asp Gly Lys Ser His Asp Val Lys Met Lys Leu Gln
            355                 360                 365

Ala Asp Asp Ser Ser Gln Leu Ser Ser Lys Thr Glu Leu Pro Ala Leu
            370                 375                 380

Asp Gly Ala Thr Leu Lys Asp Tyr Asp Ala Lys Gly Val Lys Gly Ile
385                 390                 395                 400

Glu Ile Thr Lys Ile Gln Pro Asn Ser Leu Ala Ala Gln Arg Gly Leu
                405                 410                 415

Lys Ser Gly Asp Ile Ile Gly Ile Asn Arg Gln Met Ile Glu Asn
            420                 425                 430

Ile Arg Glu Leu Asn Lys Val Leu Glu Thr Glu Pro Ser Ala Val Ala
            435                 440                 445

Leu Asn Ile Leu Arg Gly Asp Ser Asn Phe Tyr Leu Leu Val Gln
450                 455                 460

(2) INFORMATION FOR SEQ ID NO:3:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:3:

ATGAAAAAAA CACGTTTTGT ATTAAATAGT ATTGCACTTG G                    41

(2) INFORMATION FOR SEQ ID NO:4:

(i) SEQUENCE CHARACTERISTICS:
        (A) LENGTH: 37 amino acids
        (B) TYPE: amino acid
        (C) STRANDEDNESS: single
        (D) TOPOLOGY: linear (xi) SEQUENCE DESCRIPTION: SEQ ID NO:4:

Met Lys Lys Thr Arg Phe Val Leu Asn Ser Ile Ala Leu Gly Leu Ser
1               5                   10                  15
```

```
    Val Leu Ser Thr Ser Phe Val Ala Gln Ala Thr Leu Pro Ser Phe Val
                 20                  25                  30

Ser Glu Gln Asn Ser
                 35
```

(2) INFORMATION FOR SEQ ID NO:5:

(i) SEQUENCE CHARACTERISTICS:
        (A) LENGTH: 472 amino acids
        (B) TYPE: amino acid
        (C) STRANDEDNESS: single
        (D) TOPOLOGY: linear (xi) SEQUENCE DESCRIPTION: SEQ ID NO:5:

```
    Met Lys Lys Thr Thr Leu Ala Leu Ser Arg Leu Ala Leu Ser Leu Ser
    1               5                   10                  15

Leu Ala Leu Ser Pro Leu Ser Ala Thr Ala Ala Glu Thr Ser Ser Ala
                 20                  25                  30

Thr Thr Ala Gln Gln Met Pro Ser Leu Ala Pro Met Leu Glu Lys Val
                 35                  40                  45

Met Pro Ser Val Val Ser Ile Asn Val Glu Gly Ser Thr Thr Val Asn
            50                  55                  60

Thr Pro Arg Met Pro Arg Asn Phe Gln Gln Phe Phe Gly Asp Asp Ser
    65                  70                  75                  80

Pro Phe Cys Gln Glu Gly Ser Pro Phe Gln Ser Ser Pro Phe Cys Gln
                    85                  90                  95

Gly Gly Gln Gly Gly Asn Gly Gly Gln Gln Lys Phe Met Ala
                    100                 105                 110

Leu Gly Ser Gly Val Ile Ile Asp Ala Asp Lys Gly Tyr Val Val Thr
                    115                 120                 125

Asn Asn His Val Val Asp Asn Ala Thr Val Ile Lys Val Gln Leu Ser
                    130                 135                 140

Asp Gly Arg Lys Phe Asp Ala Lys Met Val Gly Lys Asp Pro Arg Ser
    145                 150                 155                 160

Asp Ile Ala Leu Ile Gln Ile Gln Asn Pro Lys Asn Leu Thr Ala Ile
                    165                 170                 175

Lys Met Ala Asp Ser Asp Ala Leu Arg Val Gly Asp Tyr Thr Val Gly
                    180                 185                 190

Ile Gly Asn Pro Phe Gly Leu Gly Glu Thr Val Thr Ser Gly Ile Val
                    195                 200                 205

Ser Ala Leu Gly Arg Ser Gly Leu Asn Ala Glu Asn Tyr Glu Asn Phe
                    210                 215                 220

Ile Gln Thr Asp Ala Ala Ile Asn Arg Gly Asn Ser Gly Gly Ala Leu
    225                 230                 235                 240

Val Asn Leu Asn Gly Glu Leu Ile Gly Ile Asn Thr Ala Ile Leu Ala
                    245                 250                 255

Pro Asp Gly Gly Asn Ile Gly Ile Gly Phe Ala Ile Pro Ser Asn Met
                    260                 265                 270

Val Lys Asn Leu Thr Ser Gln Met Val Glu Tyr Gly Gln Val Lys Arg
                    275                 280                 285

Gly Glu Leu Gly Ile Met Gly Thr Glu Leu Asn Ser Glu Leu Ala Lys
                    290                 295                 300

Ala Met Lys Val Asp Ala Gln Arg Gly Ala Phe Val Ser Gln Val Leu
    305                 310                 315                 320

Pro Asn Ser Ser Ala Ala Lys Ala Gly Ile Lys Ala Gly Asp Val Ile
                    325                 330                 335
```

```
Thr Ser Leu Asn Gly Lys Pro Ile Ser Ser Phe Ala Ala Leu Arg Ala
            340             345             350

Gln Val Gly Thr Met Pro Val Gly Ser Lys Leu Thr Leu Gly Leu Leu
            355             360             365

Arg Asp Gly Lys Gln Val Asn Val Asn Leu Glu Leu Gln Gln Ser Ser
            370             375             380

Gln Asn Gln Val Asp Ser Ser Ile Phe Asn Gly Ile Glu Gly Ala
385             390             395             400

Glu Met Ser Asn Lys Gly Lys Asp Gln Gly Val Val Asn Asn Val
            405             410             415

Lys Thr Gly Thr Pro Ala Ala Gln Ile Gly Leu Lys Lys Gly Asp Val
            420             425             430

Ile Ile Gly Ala Asn Gln Ile Ala Val Lys Asn Ile Ala Glu Ile Arg
            435             440             445

Lys Val Leu Asp Ser Lys Pro Ser Val Leu Ala Leu Asn Ile Gln Arg
            450             455             460

Gly Asp Arg His Leu Pro Val Asn
465             470
```

(2) INFORMATION FOR SEQ ID NO:6:

(i) SEQUENCE CHARACTERISTICS:
        (A) LENGTH: 475 amino acids
        (B) TYPE: amino acid
        (C) STRANDEDNESS: single
        (D) TOPOLOGY: linear (xi) SEQUENCE DESCRIPTION: SEQ ID NO:6:

```
Met Lys Lys Thr Thr Leu Ala Met Ser Ala Leu Ala Leu Ser Leu Gly
1               5               10              15

Leu Ala Leu Ser Pro Leu Ser Ala Thr Ala Ala Glu Thr Ser Ser Ser
            20              25              30

Ala Met Thr Ala Gln Gln Met Pro Ser Leu Ala Pro Met Leu Glu Lys
            35              40              45

Val Met Pro Ser Val Val Ser Ile Asn Val Glu Gly Ser Thr Thr Val
            50              55              60

Asn Thr Pro Arg Met Pro Arg Asn Phe Gln Gln Phe Gly Asp Asp
65              70              75              80

Ser Pro Phe Cys Gln Asp Gly Ser Pro Phe Gln Asn Ser Pro Phe Cys
            85              90              95

Gln Gly Gly Gly Asn Gly Gly Asn Gly Gly Gln Gln Gln Lys Phe Met
            100             105             110

Ala Leu Gly Ser Gly Val Ile Ile Asp Ala Asp Lys Gly Tyr Val Val
            115             120             125

Thr Asn Asn His Val Val Asp Asn Ala Ser Val Ile Lys Val Gln Leu
            130             135             140

Ser Asp Gly Arg Lys Phe Asp Ala Lys Val Val Gly Lys Asp Pro Arg
145             150             155             160

Ser Asp Ile Ala Leu Ile Gln Ile Gln Asn Pro Lys Asn Leu Thr Ala
            165             170             175

Ile Lys Leu Ala Asp Ser Asp Ala Leu Arg Val Gly Asp Tyr Thr Val
            180             185             190

Ala Ile Gly Asn Pro Phe Gly Leu Gly Glu Thr Val Thr Ser Gly Ile
            195             200             205

Val Ser Ala Leu Gly Arg Ser Gly Leu Asn Val Glu Asn Tyr Glu Asn
            210             215             220
```

```
Phe Ile Gln Thr Asp Ala Ala Ile Asn Arg Gly Asn Ser Gly Gly Ala
225                 230                 235                 240

Leu Val Asn Leu Asn Gly Glu Leu Ile Gly Ile Asn Thr Ala Ile Leu
            245                 250                 255

Ala Pro Asp Gly Gly Asn Ile Gly Ile Gly Phe Ala Ile Pro Ser Asn
            260                 265                 270

Met Val Lys Asn Leu Thr Ser Gln Met Val Glu Tyr Gly Gln Val Arg
            275                 280                 285

Arg Gly Glu Leu Gly Ile Met Gly Thr Glu Leu Asn Ser Glu Leu Ala
            290                 295                 300

Lys Ala Met Lys Val Asp Ala Gln Arg Gly Ala Phe Val Ser Gln Val
305                 310                 315                 320

Met Pro Asn Ser Ser Ala Ala Lys Ala Gly Ile Lys Ala Gly Asp Val
            325                 330                 335

Ile Thr Ser Leu Asn Gly Lys Pro Ile Ser Ser Phe Ala Ala Leu Arg
            340                 345                 350

Ala Gln Val Gly Thr Met Pro Val Gly Ser Lys Ile Ser Leu Gly Leu
            355                 360                 365

Leu Arg Glu Gly Lys Ala Ile Thr Val Asn Leu Glu Leu Gln Gln Ser
370                 375                 380

Ser Gln Ser Gln Val Asp Ser Ser Thr Ile Phe Ser Gly Ile Glu Gly
385                 390                 395                 400

Ala Glu Met Ser Asn Lys Gly Gln Asp Lys Gly Val Val Ser Ser
            405                 410                 415

Val Lys Ala Asn Ser Pro Ala Ala Gln Ile Gly Leu Lys Lys Gly Asp
            420                 425                 430

Val Ile Ile Gly Ala Asn Gln Ile Pro Val Lys Asn Ile Ala Glu Ile
            435                 440                 445

Arg Lys Ile Leu Asp Ser Lys Pro Ser Val Leu Ala Leu Asn Ile Gln
            450                 455                 460

Arg Gly Asp Ser Ser Ile Tyr Leu Leu Met Gln
465                 470                 475

(2) INFORMATION FOR SEQ ID NO:7:

(i) SEQUENCE CHARACTERISTICS:
        (A) LENGTH: 228 amino acids
        (B) TYPE: amino acid
        (C) STRANDEDNESS: single
        (D) TOPOLOGY: linear (xi) SEQUENCE DESCRIPTION: SEQ ID NO:7:

Ile Val Gly Gly Tyr Lys Cys Glu Lys Asn Ser Gln Pro Trp Gln Val
1               5                   10                  15

Ala Val Ile Asn Glu Tyr Leu Cys Gly Gly Val Leu Ile Asp Pro Ser
            20                  25                  30

Trp Val Ile Thr Ala Ala His Cys Tyr Ser Asn Asn Tyr Gln Val Leu
            35                  40                  45

Leu Gly Arg Asn Asn Leu Phe Lys Asp Glu Pro Phe Ala Gln Arg Arg
            50                  55                  60

Leu Val Pro Gln Ser Phe Arg His Pro Asp Tyr Ile Pro Leu Ile Pro
65                  70                  75                  80

Val His Asp His Ser Asn Asp Leu Met Leu Leu His Leu Ser Glu Pro
            85                  90                  95

Ala Asp Ile Thr Gly Gly Val Lys Val Ile Asp Leu Pro Thr Lys Glu
            100                 105                 110
```

```
Pro Lys Val Gly Ser Thr Cys Leu Ala Ser Gly Trp Gly Ser Thr Asn
            115                 120                 125
Pro Ser Glu Met Val Val Ser His Asp Leu Gln Cys Val Asn Ile His
130                 135                 140
Leu Leu Ser Asn Glu Lys Cys Ile Glu Thr Tyr Lys Asp Asn Val Thr
145                 150                 155                 160
Asp Val Met Leu Cys Ala Gly Glu Met Glu Gly Gly Lys Asp Thr Cys
                165                 170                 175
Ala Gly Asp Ser Gly Gly Pro Leu Ile Cys Asp Gly Val Leu Gln Gly
            180                 185                 190
Ile Thr Ser Gly Gly Ala Thr Pro Cys Ala Lys Pro Lys Thr Pro Ala
            195                 200                 205
Ile Tyr Ala Lys Leu Ile Lys Phe Thr Ser Trp Ile Lys Lys Val Met
210                 215                 220
Lys Glu Asn Pro
225
```

(2) INFORMATION FOR SEQ ID NO:8:

(i) SEQUENCE CHARACTERISTICS:
        (A) LENGTH: 232 amino acids
        (B) TYPE: amino acid
        (C) STRANDEDNESS: single
        (D) TOPOLOGY: linear (xi) SEQUENCE DESCRIPTION: SEQ ID NO:8:

```
Ile Ile Gly Gly Arg Glu Cys Glu Lys Asn Ser His Pro Trp Gln Val
1               5                   10                  15
Ala Ile Tyr His Tyr Ser Ser Phe Gln Cys Gly Gly Val Leu Val Asn
                20                  25                  30
Pro Lys Trp Val Leu Thr Ala Ala His Cys Lys Asn Asp Asn Tyr Glu
            35                  40                  45
Val Trp Leu Gly Arg His Asn Leu Phe Glu Asn Glu Asn Thr Ala Gln
50                  55                  60
Phe Phe Gly Val Thr Ala Asp Phe Pro His Pro Gly Phe Asn Leu Ser
65                  70                  75                  80
Ala Asp Gly Lys Asp Tyr Ser His Asp Leu Met Leu Leu Arg Leu Gln
                85                  90                  95
Ser Pro Ala Lys Ile Thr Asp Ala Val Lys Val Leu Glu Leu Pro Thr
            100                 105                 110
Gln Glu Pro Glu Leu Gly Ser Thr Cys Glu Ala Ser Gly Trp Gly Ser
            115                 120                 125
Ile Glu Pro Gly Pro Asp Asp Phe Glu Phe Pro Asp Glu Ile Gln Cys
130                 135                 140
Val Gln Leu Thr Leu Leu Gln Asn Thr Phe Cys Ala Asp Ala His Pro
145                 150                 155                 160
Asp Lys Val Thr Glu Ser Met Leu Cys Ala Gly Tyr Leu Pro Gly Gly
                165                 170                 175
Lys Asp Thr Cys Met Gly Asp Ser Gly Gly Pro Leu Ile Cys Asn Gly
            180                 185                 190
Met Trp Gln Gly Ile Thr Ser Trp Gly His Thr Pro Cys Gly Ser Ala
            195                 200                 205
Asn Lys Pro Ser Ile Tyr Thr Lys Leu Ile Phe Tyr Leu Asp Trp Ile
210                 215                 220
Asp Asp Thr Ile Thr Glu Asn Pro
225                 230
```

(2) INFORMATION FOR SEQ ID NO:9:

(i) SEQUENCE CHARACTERISTICS:
        (A) LENGTH: 223 amino acids
        (B) TYPE: amino acid
        (C) STRANDEDNESS: single
        (D) TOPOLOGY: linear (xi) SEQUENCE DESCRIPTION: SEQ ID NO:9:

```
Ile Val Gly Gly Tyr Thr Cys Gly Ala Asn Thr Val Pro Tyr Gln Val
 1               5                  10                  15

Ser Leu Asn Ser Gly Tyr His Phe Cys Gly Gly Ser Leu Ile Asn Ser
            20                  25                  30

Gln Trp Val Val Ser Ala Ala His Cys Tyr Lys Ser Gly Ile Gln Val
        35                  40                  45

Arg Leu Gly Glu Asp Asn Ile Asn Val Val Glu Gly Asn Glu Gln Phe
50                  55                  60

Ile Ser Ala Ser Lys Ser Ile Val His Pro Ser Tyr Asn Ser Asn Thr
65                  70                  75                  80

Leu Asn Asn Asp Ile Met Leu Ile Lys Leu Lys Ser Ala Ala Ser Leu
                85                  90                  95

Asn Ser Arg Val Ala Ser Ile Ser Leu Pro Thr Ser Cys Ala Ser Ala
            100                 105                 110

Gly Thr Gln Cys Leu Ile Ser Gly Trp Gly Asn Thr Lys Ser Ser Gly
        115                 120                 125

Thr Ser Tyr Pro Asp Val Leu Lys Cys Leu Lys Ala Pro Ile Leu Ser
130                 135                 140

Asp Ser Ser Cys Lys Ser Ala Tyr Pro Gly Gln Ile Thr Ser Asn Met
145                 150                 155                 160

Phe Cys Ala Gly Tyr Leu Glu Gly Gly Lys Asp Ser Cys Gln Gly Asp
                165                 170                 175

Ser Gly Gly Pro Val Val Cys Ser Gly Lys Leu Gln Gly Ile Val Ser
            180                 185                 190

Trp Gly Ser Gly Cys Ala Gln Lys Asn Lys Pro Gly Val Tyr Thr Lys
        195                 200                 205

Val Cys Asn Tyr Val Ser Trp Ile Lys Gln Thr Ile Ala Ser Asn
210                 215                 220
```

(2) INFORMATION FOR SEQ ID NO:10:

(i) SEQUENCE CHARACTERISTICS:
        (A) LENGTH: 228 amino acids
        (B) TYPE: amino acid
        (C) STRANDEDNESS: single
        (D) TOPOLOGY: linear (xi) SEQUENCE DESCRIPTION: SEQ ID NO:10:

```
Ile Val Asn Gly Glu Glu Ala Val Pro Gly Ser Trp Pro Trp Gln Val
 1               5                  10                  15

Ser Leu Gln Asp Lys Thr Gly Phe His Phe Cys Gly Gly Ser Leu Ile
            20                  25                  30

Asn Glu Asn Trp Val Val Thr Ala Ala His Cys Gly Val Thr Thr Ser
        35                  40                  45

Asp Val Val Val Ala Gly Glu Phe Asp Gln Gly Ser Ser Ser Glu Lys
50                  55                  60

Ile Gln Lys Leu Lys Ile Ala Lys Val Phe Lys Asn Ser Lys Tyr Asn
65                  70                  75                  80
```

```
Ser Leu Thr Ile Asn Asn Asp Ile Thr Leu Leu Lys Leu Ser Thr Ala
                 85                  90                  95

Ala Ser Phe Ser Gln Thr Val Ser Ala Val Cys Leu Pro Ser Ala Ser
            100                 105                 110

Asp Asp Phe Ala Ala Gly Thr Thr Cys Val Thr Thr Gly Trp Gly Leu
            115                 120                 125

Thr Arg Tyr Ala Asn Thr Pro Asp Arg Leu Gln Gln Ala Ser Leu Pro
            130                 135                 140

Leu Leu Ser Asn Thr Asn Cys Lys Lys Tyr Trp Gly Thr Lys Ile Lys
145                 150                 155                 160

Asp Ala Met Ile Cys Ala Gly Ala Ser Gly Val Ser Ser Cys Met Gly
                165                 170                 175

Asp Ser Gly Gly Pro Leu Val Cys Lys Lys Asn Gly Ala Trp Thr Leu
                180                 185                 190

Val Gly Ile Val Ser Trp Gly Ser Ser Thr Cys Ser Thr Ser Thr Pro
                195                 200                 205

Gly Val Tyr Ala Arg Val Thr Ala Leu Val Asn Trp Val Gln Gln Thr
                210                 215                 220

Leu Ala Ala Asn
225
```

(2) INFORMATION FOR SEQ ID NO:11:

(i) SEQUENCE CHARACTERISTICS:
        (A) LENGTH: 240 amino acids
        (B) TYPE: amino acid
        (C) STRANDEDNESS: single
        (D) TOPOLOGY: linear (xi) SEQUENCE DESCRIPTION: SEQ ID NO:11:

```
Val Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
                20                  25                  30

Thr Leu Ile Arg Gln Asn Trp Val Met Thr Ala Ala His Cys Val Asp
            35                  40                  45

Arg Glu Leu Thr Phe Arg Val Val Val Gly Glu His Asn Leu Asn Gln
50                  55                  60

Asn Asn Gly Thr Glu Gln Tyr Val Gly Val Gln Lys Ile Val Val His
65                  70                  75                  80

Pro Tyr Trp Asn Thr Asp Asp Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Arg Ala Gly Thr Ile Leu Ala Asn Asn Ser Pro Cys Tyr
            115                 120                 125

Ile Thr Gly Trp Gly Leu Thr Arg Thr Asn Gly Gln Leu Ala Gln Thr
            130                 135                 140

Leu Gln Gln Ala Tyr Leu Pro Thr Val Asp Tyr Ala Ile Cys Ser Ser
145                 150                 155                 160

Ser Ser Tyr Trp Gly Ser Thr Val Lys Asn Ser Met Val Cys Ala Gly
                165                 170                 175

Gly Asp Gly Val Arg Ser Gly Cys Gln Gly Asp Ser Gly Gly Pro Leu
                180                 185                 190

His Cys Leu Val Asn Gly Gln Tyr Ala Val His Gly Val Thr Ser Phe
                195                 200                 205
```

```
            Val Ser Arg Leu Gly Cys Asn Val Thr Arg Lys Pro Thr Val Phe Thr
                210                 215                 220

Arg Val Ser Ala Tyr Ile Ser Trp Ile Asn Asn Val Ile Ala Ser Asn
            225                 230                 235                 240
```

(2) INFORMATION FOR SEQ ID NO:12:

(i) SEQUENCE CHARACTERISTICS:
        (A) LENGTH: 224 amino acids
        (B) TYPE: amino acid
        (C) STRANDEDNESS: single
        (D) TOPOLOGY: linear (xi) SEQUENCE DESCRIPTION: SEQ ID NO:12:

```
            Ile Ile Gly Gly Val Glu Ser Ile Pro His Ser Arg Pro Tyr Met Ala
            1               5                   10                  15

His Leu Asp Ile Val Thr Glu Lys Gly Leu Arg Val Ile Cys Gly Gly
                            20                  25                  30

Phe Leu Ile Ser Arg Gln Phe Val Leu Thr Ala Ala His Cys Lys Gly
                        35                  40                  45

Arg Glu Ile Thr Val Ile Leu Gly Ala His Asp Val Arg Lys Arg Glu
                    50                  55                  60

Ser Thr Gln Gln Lys Ile Lys Val Glu Lys Gln Ile Ile His Glu Ser
            65                  70                  75                  80

Tyr Asn Ser Val Pro Asn Leu His Asp Ile Met Leu Leu Lys Leu Glu
                            85                  90                  95

Lys Lys Val Glu Leu Thr Pro Ala Val Asn Val Val Pro Leu Pro Ser
                        100                 105                 110

Pro Ser Asp Phe Ile His Pro Gly Ala Met Cys Trp Ala Ala Gly Trp
                    115                 120                 125

Gly Lys Thr Gly Val Arg Asp Pro Thr Ser Tyr Thr Leu Arg Glu Val
            130                 135                 140

Glu Leu Arg Ile Met Asp Glu Lys Ala Cys Val Asp Tyr Arg Tyr Tyr
                            150                 155                 160
            145

Glu Tyr Lys Phe Gln Val Cys Val Gly Ser Pro Thr Thr Leu Arg Ala
                        165                 170                 175

Ala Phe Met Gly Asp Ser Gly Gly Pro Leu Leu Cys Ala Gly Val Ala
                    180                 185                 190

His Gly Ile Val Ser Tyr Gly His Pro Asp Ala Lys Pro Pro Ala Ile
            195                 200                 205

Phe Thr Arg Val Ser Thr Tyr Val Pro Trp Ile Asn Ala Val Ile Asn
                            210                 215                 220
```

(2) INFORMATION FOR SEQ ID NO:13:

(i) SEQUENCE CHARACTERISTICS:
        (A) LENGTH: 223 amino acids
        (B) TYPE: amino acid
        (C) STRANDEDNESS: single
        (D) TOPOLOGY: linear (xi) SEQUENCE DESCRIPTION: SEQ ID NO:13:

```
            Val Val Gly Gly Thr Arg Ala Ala Gln Gly Glu Phe Pro Phe Met Val
            1               5                   10                  15

Arg Leu Ser Met Gly Cys Gly Gly Ala Leu Tyr Ala Gln Asp Ile Val
                            20                  25                  30

Leu Thr Ala Ala His Cys Val Ser Gly Ser Gly Asn Asn Thr Ser Ile
                        35                  40                  45

Thr Ala Thr Gly Gly Val Val Asp Leu Gln Ser Gly Ala Ala Val Lys
```

```
                    50                  55                  60
    Val Arg Ser Thr Lys Val Leu Gln Ala Pro Gly Tyr Asn Gly Thr Gly
    65                  70                  75                  80

Lys Asp Trp Ala Leu Ile Lys Leu Ala Gln Pro Ile Asn Gln Pro Thr
                        85                  90                  95

Leu Lys Ile Ala Thr Thr Thr Ala Tyr Asn Gln Gly Thr Phe Thr Val
                    100                 105                 110

Ala Gly Trp Gly Ala Asn Arg Glu Gly Gly Ser Gln Gln Arg Tyr Leu
                115                 120                 125

Leu Lys Ala Asn Val Pro Phe Val Ser Asp Ala Ala Cys Arg Ser Ala
            130                 135                 140

Tyr Gly Asn Glu Leu Val Ala Asn Glu Glu Ile Cys Ala Gly Tyr Pro
    145                 150                 155                 160

Asp Thr Gly Gly Val Asp Thr Cys Gln Gly Asp Ser Gly Gly Pro Met
                    165                 170                 175

Phe Arg Lys Asp Asn Ala Asp Glu Trp Ile Gln Val Gly Ile Val Ser
                    180                 185                 190

Trp Gly Tyr Gly Cys Ala Arg Pro Gly Tyr Pro Gly Val Tyr Thr Glu
                195                 200                 205

Val Ser Thr Phe Ala Ser Ala Ile Ala Ser Ala Ala Arg Thr Leu
            210                 215                 220

(2) INFORMATION FOR SEQ ID NO:14:

(i) SEQUENCE CHARACTERISTICS:
        (A) LENGTH: 185 amino acids
        (B) TYPE: amino acid
        (C) STRANDEDNESS: single
        (D) TOPOLOGY: linear (xi) SEQUENCE DESCRIPTION: SEQ ID NO:14:

Ile Ser Gly Gly Asp Ala Ile Tyr Ser Ser Thr Gly Arg Cys Ser Leu
    1               5                   10                  15

Gly Phe Asn Val Arg Ser Gly Ser Thr Tyr Tyr Phe Leu Thr Ala Gly
                    20                  25                  30

His Cys Thr Asp Gly Ala Thr Thr Trp Trp Ala Asn Ser Ala Arg Thr
                35                  40                  45

Thr Val Leu Gly Thr Thr Ser Gly Ser Ser Phe Pro Asn Asn Asp Tyr
    50                  55                  60

Gly Ile Val Arg Tyr Thr Asn Thr Thr Ile Pro Lys Asp Gly Thr Val
    65                  70                  75                  80

Gly Gly Gln Asp Ile Thr Ser Ala Ala Asn Ala Thr Val Gly Met Ala
                    85                  90                  95

Val Thr Arg Arg Gly Ser Thr Thr Gly Thr His Ser Gly Ser Val Thr
                    100                 105                 110

Ala Leu Asn Ala Thr Val Asn Tyr Gly Gly Gly Asp Val Val Tyr Gly
                115                 120                 125

Met Ile Arg Thr Asn Val Cys Ala Glu Pro Gly Asp Ser Gly Gly Pro
    130                 135                 140

Leu Tyr Ser Gly Thr Arg Ala Ile Gly Leu Thr Ser Gly Gly Ser Gly
    145                 150                 155                 160

Asn Cys Ser Ser Gly Gly Thr Thr Phe Phe Gln Pro Val Thr Glu Ala
                    165                 170                 175

Leu Val Ala Tyr Gly Val Ser Val Tyr
                    180                 185
```

(2) INFORMATION FOR SEQ ID NO:15:

(i) SEQUENCE CHARACTERISTICS:
        (A) LENGTH: 181 amino acids
        (B) TYPE: amino acid
        (C) STRANDEDNESS: single
        (D) TOPOLOGY: linear (xi) SEQUENCE DESCRIPTION: SEQ ID NO:15:

```
Ile Ala Gly Gly Glu Ala Ile Thr Thr Gly Gly Ser Arg Cys Ser Leu
 1               5                  10                  15

Gly Phe Asn Val Ser Val Asn Gly Val Ala His Ala Leu Thr Ala Gly
             20                  25                  30

His Cys Thr Asn Ile Ser Ala Ser Trp Ser Ile Gly Thr Arg Thr Gly
         35                  40                  45

Thr Ser Phe Pro Asn Asn Asp Tyr Gly Ile Ile Arg His Ser Asn Pro
 50                  55                  60

Ala Ala Ala Asp Gly Arg Val Tyr Leu Tyr Asn Gly Ser Tyr Gln Asp
65                  70                  75                  80

Ile Thr Thr Ala Gly Asn Ala Phe Val Gly Gln Ala Val Gln Arg Ser
                 85                  90                  95

Gly Ser Thr Thr Gly Leu Arg Ser Gly Ser Val Thr Gly Leu Asn Ala
            100                 105                 110

Thr Val Asn Tyr Gly Ser Ser Gly Ile Val Tyr Gly Met Ile Gln Thr
        115                 120                 125

Asn Val Cys Ala Gln Pro Gly Asp Ser Gly Gly Ser Leu Phe Ala Gly
130                 135                 140

Ser Thr Ala Leu Gly Leu Thr Ser Gly Gly Ser Gly Asn Cys Arg Thr
145                 150                 155                 160

Gly Gly Thr Thr Phe Tyr Gln Pro Val Thr Glu Ala Leu Ser Ala Tyr
                165                 170                 175

Gly Ala Thr Val Leu
                180
```

(2) INFORMATION FOR SEQ ID NO:16:

(i) SEQUENCE CHARACTERISTICS:
        (A) LENGTH: 198 amino acids
        (B) TYPE: amino acid
        (C) STRANDEDNESS: single
        (D) TOPOLOGY: linear (xi) SEQUENCE DESCRIPTION: SEQ ID NO:16:

```
Ala Asn Ile Val Gly Gly Ile Glu Tyr Ser Ile Asn Asn Ala Ser Leu
 1               5                  10                  15

Cys Ser Val Gly Phe Ser Val Thr Arg Gly Ala Thr Lys Gly Phe Val
             20                  25                  30

Thr Ala Gly His Cys Gly Thr Val Asn Ala Thr Ala Arg Ile Gly Gly
         35                  40                  45

Ala Val Val Gly Thr Phe Ala Ala Arg Val Phe Pro Gly Asn Asp Arg
 50                  55                  60

Ala Trp Val Ser Leu Thr Ser Ala Gln Thr Leu Leu Pro Arg Val Ala
65                  70                  75                  80

Asn Gly Ser Ser Phe Val Thr Val Arg Gly Ser Thr Glu Ala Ala Val
                 85                  90                  95

Gly Ala Ala Val Cys Arg Ser Gly Arg Thr Thr Gly Tyr Gln Cys Gly
            100                 105                 110

Thr Ile Thr Ala Lys His Val Thr Ala Asn Tyr Ala Glu Gly Ala Val
        115                 120                 125
```

```
        Arg Gly Leu Thr Gln Gly Asn Ala Cys Met Gly Arg Gly Asp Ser Gly
            130                 135                 140

Gly Ser Trp Ile Thr Ser Ala Gly Gln Ala Gln Gly Val Met Ser Gly
        145                 150                 155                 160

Gly Asn Val Gln Ser Asn Gly Asn Asn Cys Gly Ile Pro Ala Ser Gln
                        165                 170                 175

Arg Ser Ser Leu Phe Glu Arg Leu Gln Pro Ile Leu Ser Gln Tyr Gly
                    180                 185                 190

Leu Ser Leu Val Thr Gly
                    195
```

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:17:

```
        Gly Asn Ser Gly Gly Ala Leu
        1               5
```

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:18:

```
        Gly Asp Ser Gly Gly Pro Lys
        1               5
```

(2) INFORMATION FOR SEQ ID NO:19:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:19:

```
        Met Lys Lys Thr Arg Phe Val Leu Asn Ser Ile Ala Leu Gly
        1               5                   10
```

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:20:

CGCTCCACCA GCATTACCGC GG                      22

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:21:

ATCAATAACA GCATTATTGG T                                                         21

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:22:

TAATGCAATT GCTGATAGTT C                                                         21

(2) INFORMATION FOR SEQ ID NO:23:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:23:

Lys Phe Phe Phe Gly Asp Arg Phe Ala Glu Gln
    1               5                   10